United States Patent
Babu

(10) Patent No.: US 11,345,927 B2
(45) Date of Patent: May 31, 2022

(54) COMPOSITIONS FOR REDUCING SARCOLIPIN EXPRESSION AND PREVENTING AND TREATING MUSCULAR DYSTROPHY AND CARDIOMYOPATHY AND METHODS OF USE

(71) Applicant: Rutgers, The State University of New Jersey, New Brunswick, NJ (US)

(72) Inventor: Gopal J. Babu, Randolph, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/479,838

(22) PCT Filed: Jan. 22, 2018

(86) PCT No.: PCT/US2018/014709
§ 371 (c)(1),
(2) Date: Jul. 22, 2019

(87) PCT Pub. No.: WO2018/136880
PCT Pub. Date: Jul. 26, 2018

(65) Prior Publication Data
US 2021/0163984 A1  Jun. 3, 2021

Related U.S. Application Data

(60) Provisional application No. 62/589,273, filed on Nov. 21, 2017, provisional application No. 62/575,089, filed on Oct. 20, 2017, provisional application No. 62/449,371, filed on Jan. 23, 2017.

(51) Int. Cl.
*C12N 15/86* (2006.01)
*C12N 15/113* (2010.01)
*C12Q 1/68* (2018.01)

(52) U.S. Cl.
CPC ............ *C12N 15/86* (2013.01); *C12N 15/113* (2013.01); *C12N 2310/531* (2013.01); *C12N 2320/32* (2013.01); *C12N 2750/14141* (2013.01)

(58) Field of Classification Search
None
See application file for complete search history.

(56) References Cited

U.S. PATENT DOCUMENTS

2016/0303255 A1   10/2016  Passananti et al.
2017/0065685 A1*  3/2017   Hajjar ............ C12Y 306/01003

FOREIGN PATENT DOCUMENTS

EP   3085785 A1    10/2016
WO   2016115543 A2  7/2016

OTHER PUBLICATIONS

Seth, et al: "Dynamic Regulation of SR Ca2+ Stores by STIM1 and Sarcolipin During Muscle Differentiation", Dev Dyn. Apr. 2012, vol. 241, No. 4, pp. 639-647.
Genbank_AC122545: "Mus Musculus Chromosome 5, Clone RP23-324H16, Complete Sequence", GenBank Accession No. AC122545, Dec. 21, 2005 [online], [Retrieved on Mar. 12, 2018], Retrieved from the Internet <URL: https://www.ncbi.nlm.nih.gov/nuccore/AC122545>, Locus: Accession Source; and Origin), the Region between Nucleotides 7113-7160.
Schneider, et al: "Increased Sarcolipin Expression and Decreased Sarco(endo)plasmmic Reticulum Ca2+ Uptake in Skeletal Muscles of Mouse Models of Duchenne Muscular Dystrophy", J. Muscle Res. Cell Motil, 2013, vol. 34, pp. 349-356.
Schinkel et al: "Long-Term Preservation of Cardiac Structure and Function After Adeno-Associated Virus Serotype 9-Mediated Microdystrophin Gene Transfer in mdx Mice", Human Gene Therapy, Jun. 2012, vol. 23, No. 6, pp. 566-575.
Yang et al: "AAV-Based shRNA Silencing of NF-kB Ameliorates Muscle Pathologies in mdx Mice", Gene Therapy, 2012, vol. 19, pp. 1196-1204.
Liu, et al: "GW27-e1130 Effect of Sarcolipin Silencing in Attenuating Ventricular Arrhythmias in Diabetic Cardiomyopathy", Journal fo the American College of Cardiology, Oct. 2016, vol. 68, No. 16, XP029762266.
Voit, et al: "Reducing Sarcolipin Expression Mitigates Duchenne Muscular Dystrophy and Associated Cardiomyopathy in Mice", Nature Communications, Oct. 20, 2017, vol. 8, No. 1, XP055741575.

* cited by examiner

*Primary Examiner* — Sean McGarry
(74) *Attorney, Agent, or Firm* — Fox Rothschild LLP

(57) ABSTRACT

Compositions, recombinant viruses, and recombinant viral vectors for inhibiting sarcolipin (SLN) expression or activity in a cell and for preventing or treating Duchenne Muscular Dystrophy (DMD) in a subject (e.g., a human patient having or predisposed to having DMD) and in some embodiments additionally cardiomyopathy, include a therapeutically effective amount of an inhibitor of SLN. Methods of using these compositions, recombinant viruses, and recombinant viral vectors are also described herein. These compositions, recombinant viruses, and recombinant viral vectors and methods of use provide novel therapies for DMD and associated cardiomyopathy based on the reduction of SLN expression and/or activity.

5 Claims, 26 Drawing Sheets
Specification includes a Sequence Listing.

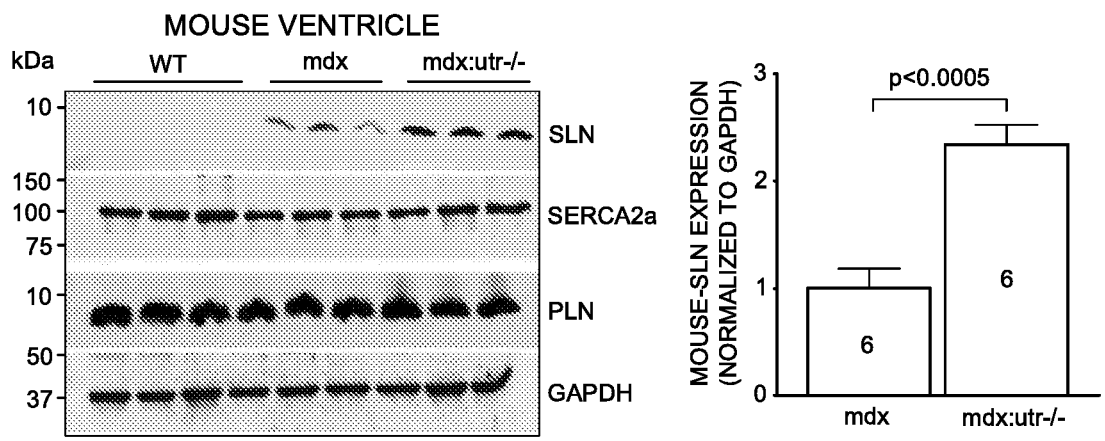
Figure 1a
Figure 1b
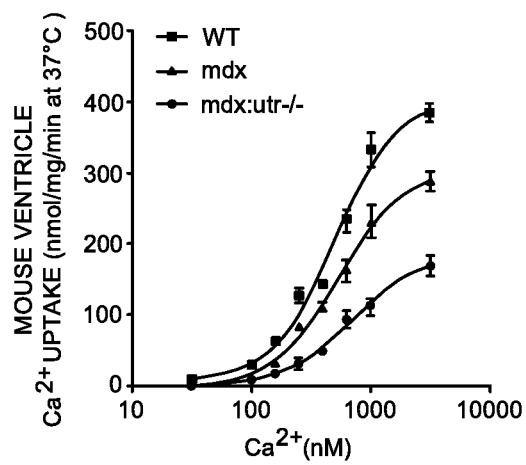
Figure 1c
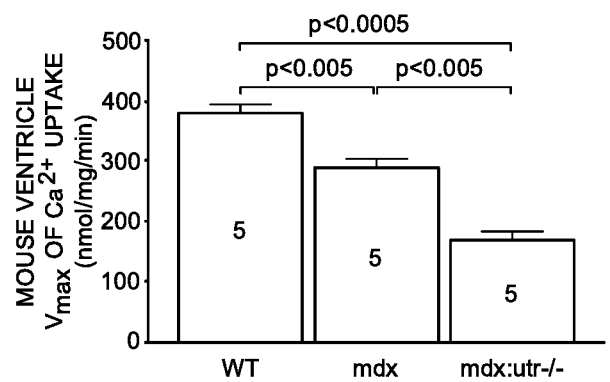
Figure 1d
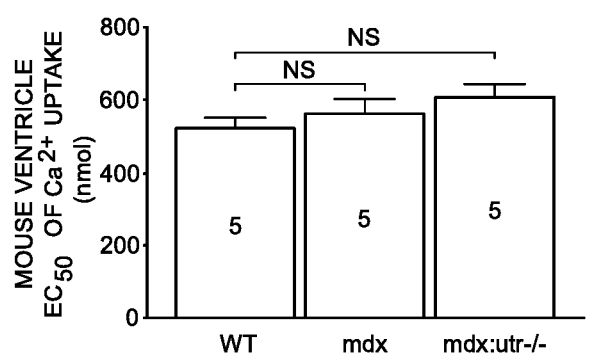
Figure 1e

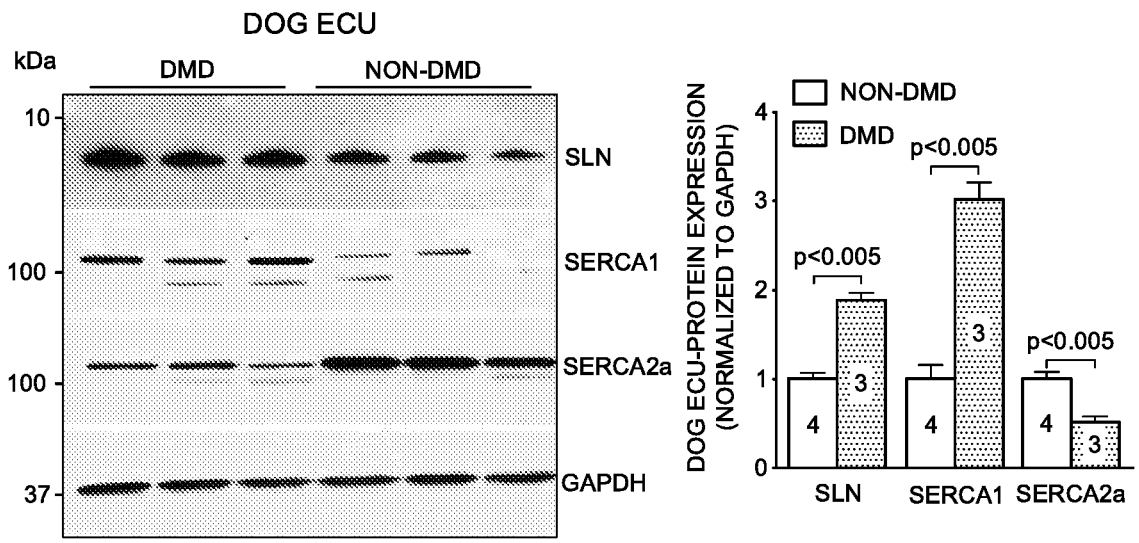
Figure 2a
Figure 2b
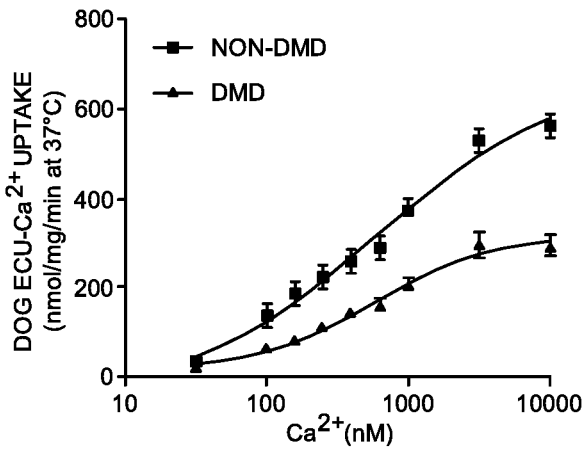
Figure 2c
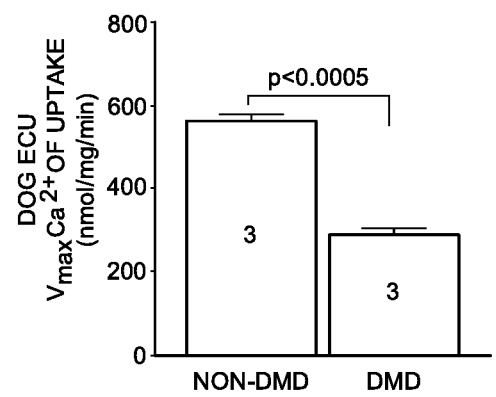
Figure 2d
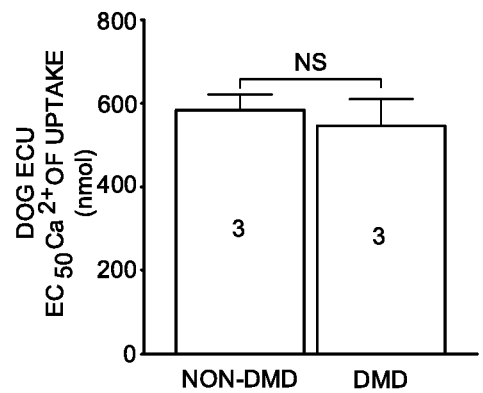
Figure 2e

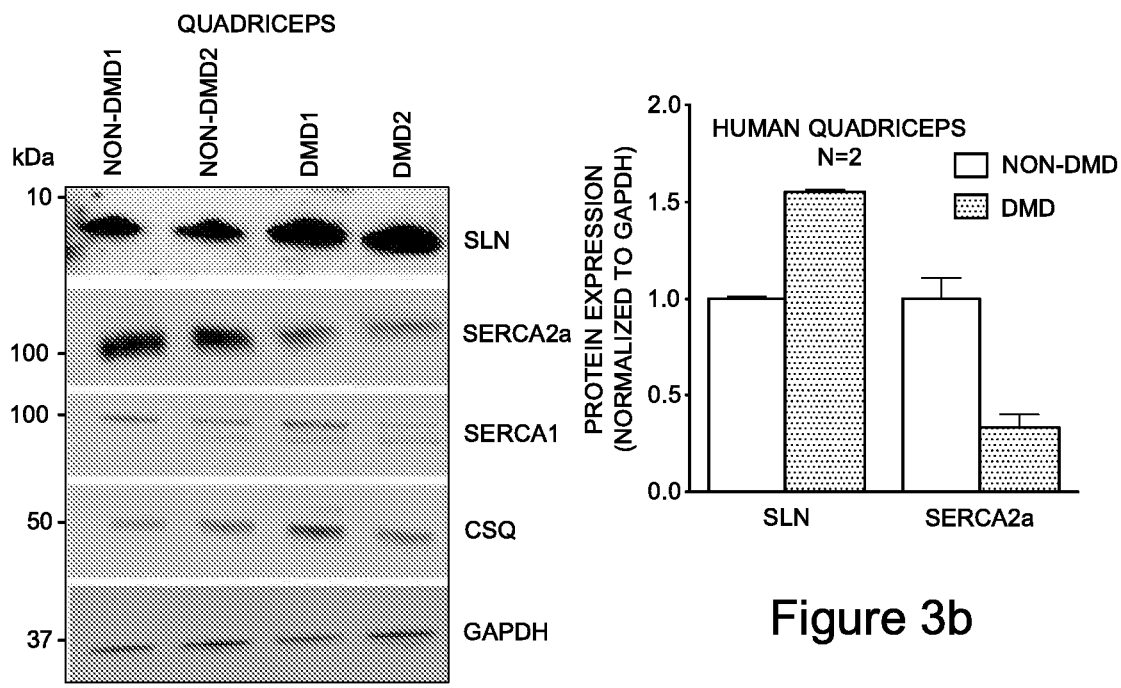
Figure 3a
Figure 3b
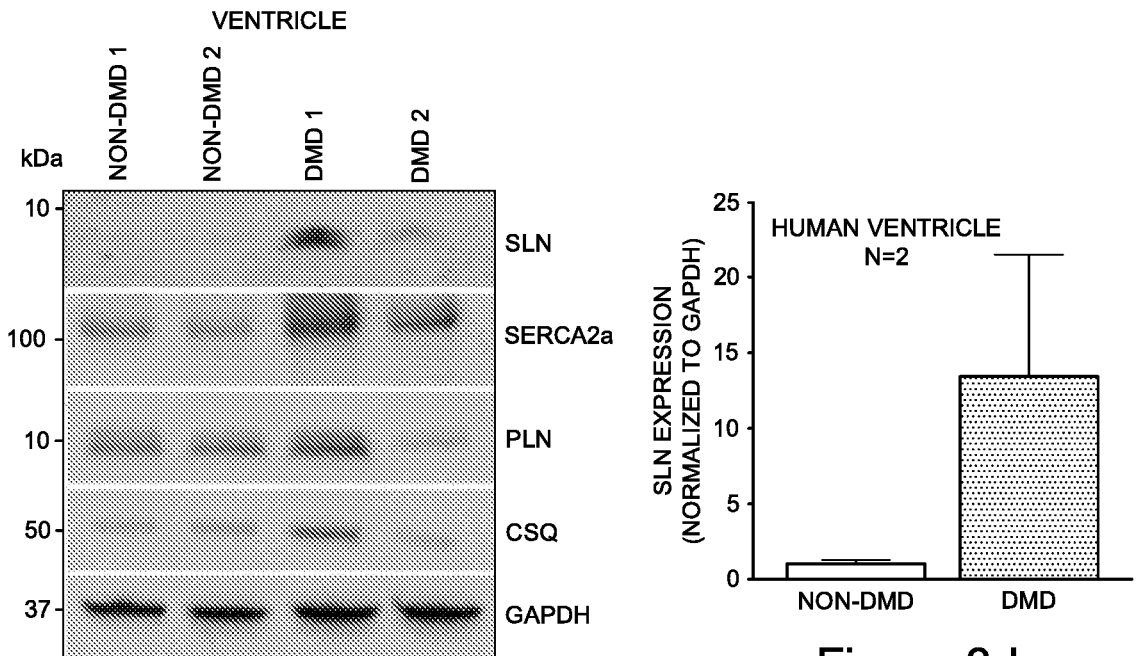
Figure 3c
Figure 3d

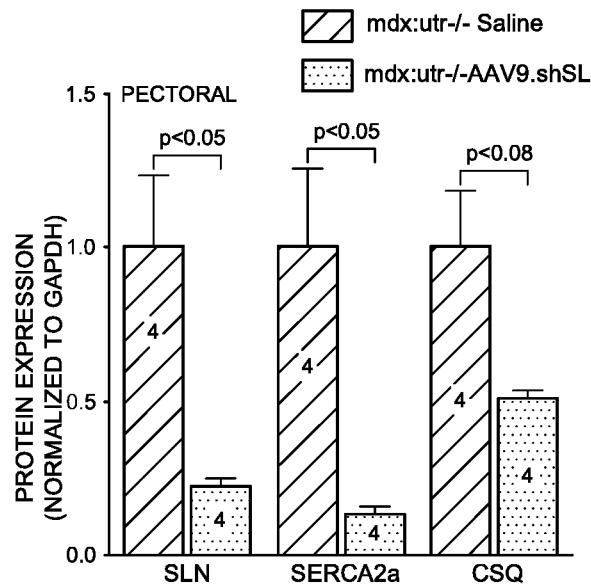
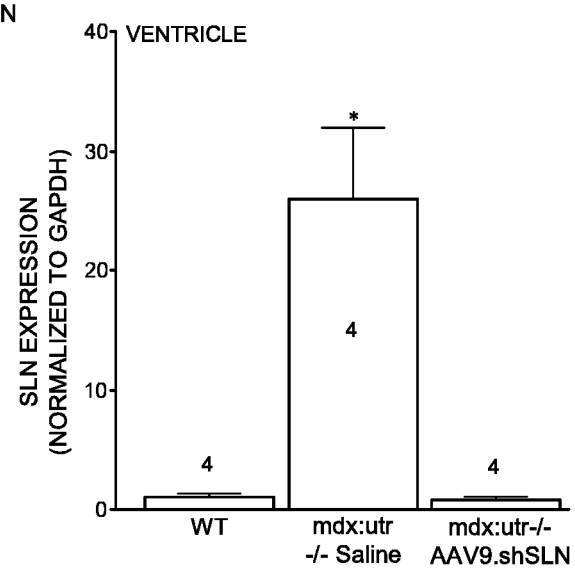
Figure 12a
Figure 12b
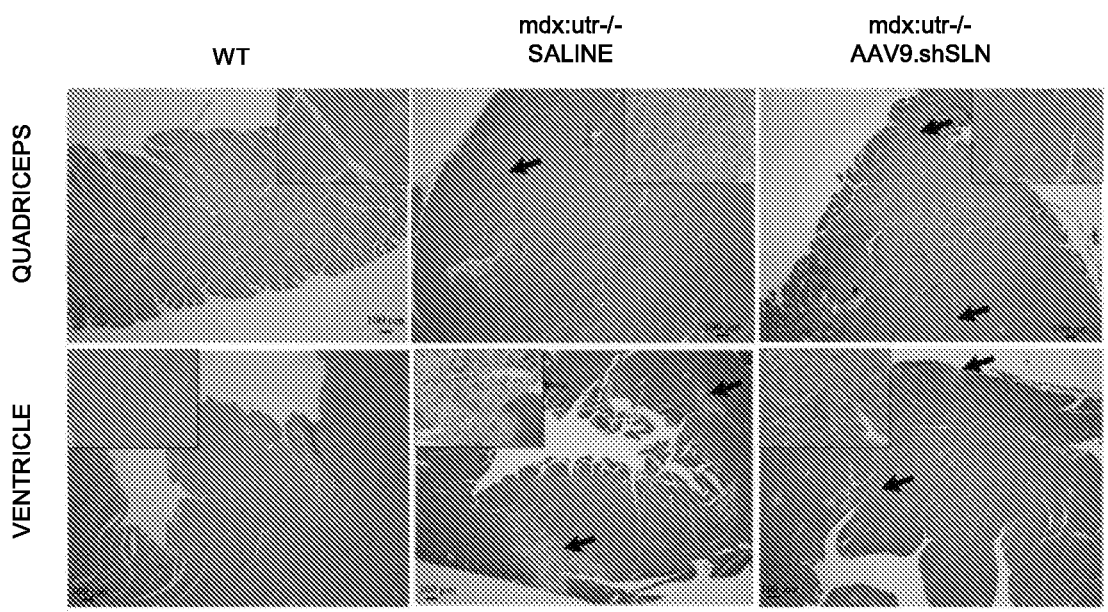
Figure 12c

SEQUENCE LISTING

```
<160> NUMBER OF SEQ ID NOS: 12

<210> SEQ ID NO 1
<211> LENGTH: 31
<212> TYPE: PRT
<213> ORGANISM: HOMO SAPIENS

<400> SEQUENCE: 1

Met Gly Ile Asn Thr Arg Glu Leu Phe Leu Asn Phe Thr Ile Val Leu
1               5                   10                  15

Ile Thr Val Ile Leu Met Trp Leu Leu Val Arg Ser Tyr Gly Tyr
            20                  25                  30

<210> SEQ ID NO 2
<211> LENGTH: 47
<212> TYPE: DNA
<213> ORGANISM: Artificial Sequence
<220> FEATURE:
<223> OTHER INFORMATION: SYNTHETIC CONSTRUCT

<400> SEQUENCE: 2
acttcacagt tgtcctcatc actcgagtga tgaggacaac tgtgaag                47

<210> SEQ ID NO 3
<211> LENGTH: 16
<212> TYPE: DNA
<213> ORGANISM: Artificial Sequence
<220> FEATURE:
<223> OTHER INFORMATION: SYNTHETIC CONSTRUCT

<400> SEQUENCE: 3
tgccttcctt gaccct                                                  16
```

<210> SEQ ID NO 4
<211> LENGTH: 16
<212> TYPE: DNA
<213> ORGANISM: Artificial Sequence
<220> FEATURE:
<223> OTHER INFORMATION: SYNTHETIC CONSTRUCT

<400> SEQUENCE: 4
ccttgctgtc ctgccc                                             16

<210> SEQ ID NO 5
<211> LENGTH: 55
<212> TYPE: DNA
<213> ORGANISM: Artificial Sequence
<220> FEATURE:
<223> OTHER INFORMATION: SYNTHETIC CONSTRUCT

<400> SEQUENCE: 5
ctgtttctca acttcactat tgtttcaaga gaacaatagt gaagttgaga aacag    55

<210> SEQ ID NO 6
<211> LENGTH: 55
<212> TYPE: DNA
<213> ORGANISM: Artificial Sequence
<220> FEATURE:
<223> OTHER INFORMATION: SYNTHETIC CONSTRUCT

<400> SEQUENCE: 6
ctgtgaaaat ggggataaac accttcaaga gaggtgttta tccccatttt cacag    55

<210> SEQ ID NO 7
<211> LENGTH: 48
<212> TYPE: DNA
<213> ORGANISM: Artificial Sequence
<220> FEATURE:
<223> OTHER INFORMATION: SYNTHETIC CONSTRUCT

<400> SEQUENCE: 7
gtcttgatta cggttattct tctcgagaag aataaccgta atcaagac             48

<210> SEQ ID NO 8
<211> LENGTH: 48
<212> TYPE: DNA
<213> ORGANISM: Artificial Sequence
<220> FEATURE:
<223> OTHER INFORMATION: SYNTHETIC CONSTRUCT

<400> SEQUENCE: 8
gttattctta tgtggctcct tctcgagaag gagccacata agaataac             48

<210> SEQ ID NO 9
<211> LENGTH: 48
<212> TYPE: DNA
<213> ORGANISM: Artificial Sequence
<220> FEATURE:
<223> OTHER INFORMATION: SYNTHETIC CONSTRUCT

<400> SEQUENCE: 9
tctcaacttc actattgtct tctcgagaag acaatagtga agttgaga             48

<210> SEQ ID NO 10
<211> LENGTH: 47
<212> TYPE: DNA
<213> ORGANISM: Artificial Sequence
<220> FEATURE:
<223> OTHER INFORMATION: SYNTHETIC CONSTRUCT

```
<400> SEQUENCE: 10
actattgtct tgattacggt tctcgagaac cgtaatcaag acaatag                47

<210> SEQ ID NO 11
<211> LENGTH: 48
<212> TYPE: DNA
<213> ORGANISM: Artificial Sequence
<220> FEATURE:
<223> OTHER INFORMATION: SYNTHETIC CONSTRUCT

<400> SEQUENCE: 11
gctccttgtg aggtcctatc actcgagtga taggacctca caaggagc              48

<210> SEQ ID NO 12
<211> LENGTH: 738
<212> TYPE: DNA
<213> ORGANISM: Homo sapiens

<400> SEQUENCE: 12
agtccagaca gcctgggagg ggagaaggag ttggagctca agttggagac agcgaggaga      60
aacctgccat agccagggtg tgtctttgat cctcttcagg aggtgaggag aagccagagg     120
tccttggtgt gccctcagaa atctgcctgc agttctcacc aagccgctgt gaaaatgggg     180
ataaacaccc gggagctgtt tctcaacttc actattgtct tgattacggt tattcttatg     240
tggctccttg tgaggtccta tcagtactga gaggccatgc catggtcctg ggattgactg     300
agatgctccg gagctgcctg ctctatgccc tgagacccca ctgctgtcat tgtcacagga     360
tgccattctc catccgaggg cacctgtgac ctgcactcac aatatctgct atgctgtagt     420
gctaggattg attatgtgtt ctccaaagat gctgctccca agggctgcca agtgtttgcc     480
agggaacggt agatttattc cccaactctt aactgaaaat gtgttagaca agccacaaag     540
ttaaaattaa actggattca tgatgatgta ggattgttac aagcccctga tctgtctcac     600
cacacatccc ttcaacccac acggtctgca accaaactct aattcaacct gccagaagga     660
atgttagagg aagtctttgt cagcccttat agctatcatg tgaataaagt taagtcaact     720
tcaaaaacaa aaaaaaaa                                                  738
```

COMPOSITIONS FOR REDUCING SARCOLIPIN EXPRESSION AND PREVENTING AND TREATING MUSCULAR DYSTROPHY AND CARDIOMYOPATHY AND METHODS OF USE

CROSS-REFERENCE TO RELATED APPLICATIONS

This application claims the benefit of U.S. Provisional Application No. 62/449,371 filed Jan. 23, 2017, U.S. Provisional Application No. 62/575,089 filed Oct. 20, 2017, and U.S. Provisional Application No. 62/589,273 filed Nov. 21, 2017, the disclosures of which are incorporated herein by reference in their entireties.

FEDERALLY SPONSORED RESEARCH

This invention was made with government support under grant no. 1R01AR069107-01A1 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 22, 2018, is named 096738-00567_ST25.txt and is 3.7 kilobytes in size.

FIELD OF THE INVENTION

The invention relates generally to the fields of medicine, molecular biology, and virology. In particular, the invention relates to compositions, vectors, viruses, kits and methods for reducing sarcolipin (SLN) expression in a cell and preventing and treating Duchenne muscular dystrophy (DMD) and associated cardiomyopathy in a subject.

BACKGROUND

DMD, the most common and severe form of muscular dystrophy, is an X-linked disease caused by deficiency of dystrophin protein in muscle. DMD is a debilitating disease that affects approximately 1 in 3,600 males. It is a form of muscular dystrophy characterized by muscle weakness, loss of ambulation and eventual respiratory and cardiac implications (succumbing to respiratory and cardiac failure) that result in death by late teens or early twenties. Although DMD is primarily categorized as a neuromuscular disorder, heart disease plays a crucial role in the etiology. Almost all DMD patients show clinical cardiac symptoms, especially during the second decade of life. Although respiratory support has improved, cardiomyopathy (leading to heart failure and arrhythmias) has become an increasingly important source of morbidity and mortality. There is currently no cure for DMD. Therapeutic strategies including restoring dystrophin expression, exon skipping, stem cell replacement therapy, analog up-regulation and gene replacement face major challenges targeting the respiratory and cardiac tissues and fibrosis. Thus there is a need for new therapies that prevent or slowdown the progression of the disease in DMD patients.

Accumulated evidence suggests that abnormal elevation of intracellular $Ca^{2+}$ ($Ca^{2+}i$) is an important, early pathogenic event that initiates and perpetuates disease progression in DMD. The normal function of sarco/endoplasmic reticulum $Ca^{2+}$ ATPase (SERCA) pump accounts for ≥70% of $Ca^{2+}$ removal from the cytosol and proper muscle contraction. Reduction in SERCA activity therefore has been considered as a primary cause of $Ca^{2+}i$ overload and muscle dysfunction in DMD.

SUMMARY

Described herein are compositions, vectors, viruses, kits and methods for decreasing SLN expression or activity in a subject (e.g., a subject with DMD, cardiomyopathy, or DMD and cardiomyopathy) and preventing, ameliorating, or treating DMD and in some embodiments, also cardiomyopathy, in a subject. The compositions, vectors, viruses, kits and methods all include an inhibitor of SLN expression or activity. SLN is an inhibitor of SERCA pump. It was discovered that SLN is abnormally elevated in the muscle of DMD patients and animal models, that SLN upregulation is a molecular basis for SERCA dysfunction in both skeletal and cardiac muscles of DMD, and that SLN is a therapeutic target for the treatment of diaphragm and skeletal muscle pathology and cardiomyopathy in DMD. The experimental results described herein demonstrate that in the more severe, dystrophin/utrophin double deficient (mdx:utr−/−) mouse model of DMD, germline inactivation of one allele of the SLN gene normalized SLN expression, restored SERCA function, mitigated skeletal muscle and cardiac pathology, improved muscle regeneration, and extended life-span by ~5 times. To translate these findings into a therapeutic strategy, SLN expression was knocked down in one-month-old mdx:utr−/− mice via AAV-mediated RNA interference. The rAAV treatment markedly reduced SLN expression, attenuated muscle pathology and improved the diaphragm, skeletal muscle and cardiac function. These data show that SLN reduction is a therapeutic approach for DMD.

Accordingly, described herein is a recombinant AAV (rAAV) including a rAAV vector including a heterologous polynucleotide sequence including a nucleic acid sequence encoding a shRNA specific for sarcolipin (SLN) in a therapeutically effective amount for decreasing SLN expression or activity in a cell. The nucleic acid sequence can be, for example, one of: SEQ ID NO:7, SEQ ID NO:8, SEQ ID NO:9, SEQ ID NO:10, and SEQ ID NO:11. The rAAV can be, for example, serotype 9 (AAV9).

Also described herein are compositions including any of these rAAV. A composition as described herein can further include a second rAAV including a second rAAV vector including a heterologous polynucleotide sequence including a nucleic acid sequence encoding μ-dys. The second rAAV can be, for example, serotype 9 (AAV9).

Further described herein is a composition including a recombinant virus including a recombinant viral vector including a heterologous polynucleotide sequence including a nucleic acid sequence encoding a shRNA specific for SLN in a therapeutically effective amount for decreasing SLN expression or activity in a cell. The composition can further include a second recombinant virus including a second recombinant viral vector including a heterologous polynucleotide sequence including a nucleic acid sequence encoding μ-dys.

Yet further described herein is a method of reducing SLN expression in a cell. The method includes contacting the cell with any rAAV as described herein.

Also described herein is a method of preventing or treating Duchenne Muscular Dystrophy (DMD) in a subject (e.g., a mammal). The method includes administering to the subject any rAAV as described herein. In a typical embodiment, administration of any of the rAAV described herein prevents or treats associated cardiomyopathy in the subject. In the method, an rAAV or composition as described herein can be administered to the subject, for example, prior to onset of DMD symptoms or pathology. In the method, the subject (e.g., mammal) is administered the rAAV or the composition via, for example, injection.

Still further described herein is a method of treating cardiomyopathy in a subject (e.g., a mammal). The method includes administering to the subject a rAAV or composition as described herein.

Also described herein is a kit for reducing SLN expression in a cell or preventing or treating DMD in a subject. The kit includes: one or more rAAV as described herein, or a composition as described herein; instructions for use; and packaging.

As used herein, "protein" and "polypeptide" are used synonymously to mean any peptide-linked chain of amino acids, regardless of length or post-translational modification, e.g., glycosylation, phosphorylation, acetylation or nitrosylation.

By the terms "sarcolipin protein," "SLN protein," "sarcolipin polypeptide" and "SLN polypeptide" is meant an expression product of a SLN gene such as the native human SLN protein [MGINTRELFLNFTIVLITVILMWLL-VRSYGY] (SEQ ID NO:1), accession number, NP_003054.1. or a protein that shares at least 65% (but preferably 75, 80, 85, 90, 95, 96, 97, 98, or 99%) amino acid sequence identity with the foregoing and displays a functional activity of a native SLN protein. A "functional activity" of a protein is any activity associated with the physiological function of the protein. For example, functional activities of a native SLN protein may include: phosphorylation, dephosphorylation, nitrosylation and/or ubiquitination of SLN.

"Purified," as used herein, means separated from many other compounds or entities. A compound or entity (e.g., nucleic acid, protein, virus, viral vector) may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%.

The phrases "isolated" or "biologically pure" refer to material which is substantially or essentially free from components which normally accompany it as found in its native state.

As used herein, the phrases "SLN overexpression", "overexpression of SLN" and "abnormal elevation of SLN" are used interchangeably to mean increased levels of SLN mRNA and protein expression as compared to normal levels or normal tissues.

By the term "gene" is meant a nucleic acid molecule that codes for a particular protein, or in certain cases, a functional or structural RNA (ribonucleic acid) molecule.

As used herein, a "nucleic acid" or a "nucleic acid molecule" means a chain of two or more nucleotides such as RNA and DNA (deoxyribonucleic acid).

As used herein, the phrase "expression control sequence" refers to a nucleic acid that regulates the replication, transcription and translation of a coding sequence in a recipient cell. Examples of expression control sequences include promoter sequences, polyadenylation (pA) signals, introns, transcription termination sequences, enhancers, upstream regulatory domains, origins of replication, and internal ribosome entry sites ("IRES"). The term "promoter" is used herein to refer to a DNA regulatory sequence to which RNA polymerase binds, initiating transcription of a downstream (3' direction) coding sequence.

As used herein, the terms "operable linkage" and "operably linked" refers to a physical or functional juxtaposition of the components so described as to permit them to function in their intended manner. In the example of an expression control element in operable linkage with a nucleic acid, the relationship is such that the control element modulates expression of the nucleic acid.

By the terms "SLN gene," "SLN polynucleotide," and "SLN nucleic acid" is meant a native human SLN-encoding nucleic acid sequence, e.g., the native human SLN gene (RefSeq Accession: NM_003063.2). a nucleic acid having sequences from which a SLN cDNA can be transcribed; and/or allelic variants and homologs of the foregoing. The terms encompass double-stranded DNA, single-stranded DNA, and RNA.

As used herein, the terms "shRNA" and "short hairpin RNA" mean any artificial RNA molecule with a tight hairpin turn that can be used to silence target gene expression via RNA interference (RNAi). ShRNA is encompassed by the terms "interfering RNA" and "RNA interference molecule."

A "vector" is a composition of matter which can be used to deliver a nucleic acid of interest to the interior of a cell, including a nucleic acid molecule capable of transporting another nucleic acid to which it has been linked. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, AAV vectors, retroviral vectors, lentiviral vectors, adenoviral vectors, and the like. An expression construct can be replicated in a living cell, or it can be made synthetically. Vectors capable of directing the expression of genes to which they are operatively linked are often referred to as "expression vectors." For purposes of this application, the terms "expression construct," "expression vector," and "vector," are used interchangeably to demonstrate the application of the invention in a general, illustrative sense, and are not intended to limit the invention.

A recombinant "viral vector" is derived from the wild type genome of a virus (e.g., AAV), by using molecular methods to remove the wild type genome from the virus, and replacing it with a non-native nucleic acid, such as a heterologous polynucleotide sequence (e.g., a therapeutic gene or other therapeutic nucleic acid expression cassette). A "recombinant AAV vector" or "rAAV vector" or "rAAV vector genome" is derived from the wild type genome of AAV. Typically, for AAV, one or both inverted terminal repeat (ITR) sequences of the wild type AAV genome are retained in the rAAV vector. A recombinant viral vector (e.g., rAAV) sequence can be packaged into a virus (also referred to herein as a "particle" or "virion") for subsequent infection (transformation) of a cell, ex vivo, in vitro or in vivo. Where a rAAV vector sequence is encapsidated or packaged into an AAV particle, the particle can be referred to as a "rAAV." Such particles or virions will typically include proteins that encapsidate or package the vector genome. Particular examples include viral envelope proteins, and in the case of AAV, capsid proteins (VP1, VP2, VP3). In the experiments described herein, the rAAV tested was AAV9.shSLN. As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Recombinant vectors (e.g., rAAV vectors or plasmids), recombinant viruses or virions (recombinant viral particles), as well as methods and uses thereof, include any viral strain or serotype. A rAAV vector can be based upon an AAV serotype genome distinct from one or more of the capsid proteins that package the vector. rAAV (particles) including rAAV vectors (e.g., recombinant viral genomes) can include at least one capsid protein from a different serotype, a mixture of serotypes, or hybrids or chimeras of different serotypes, such as a VP1, VP2 or VP3 capsid protein of AAV1, AAV2, AAV3, AAV4, AAV5, AAV6, AAV7, AAV8, AAV9, AAV10, AAV11, or Rh10 serotype.

The terms "patient," "subject" and "individual" are used interchangeably herein, and mean a mammalian (e.g., human) subject to be treated, diagnosed, and/or to obtain a biological sample from. Typically, the subject is affected or likely to be affected with DMD and in some embodiments, DMD and associated cardiomyopathy and dystrophic cardiomyopathy. In a particular embodiment, a subject is a human male adolescent. In another particular embodiment, a subject is a human male adult.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der waals).

The term "labeled," with regard to a nucleic acid, peptide, polypeptide, cell, probe or antibody, is intended to encompass direct labeling of the nucleic acid, peptide, polypeptide, cell, probe or antibody by coupling (i.e., physically linking) a detectable substance to the nucleic acid, peptide, polypeptide, cell, probe or antibody.

When referring to a nucleic acid molecule or polypeptide, the term "native" refers to a naturally-occurring (e.g., a wild-type (WT)) nucleic acid or polypeptide.

As used herein, the term "therapeutic agent" is meant to encompass any molecule, chemical entity, composition, drug, or biological agent capable of curing, healing, alleviating, relieving, altering, remedying, ameliorating, improving or affecting a disease, the symptoms of disease, or the predisposition toward disease. The term "therapeutic agent" includes shRNA, small molecules, antisense reagents, nucleic acids, siRNA, antibodies, enzymes, polypeptides, peptides, recombinant viruses, organic or inorganic molecules, natural or synthetic compounds and the like.

As used herein, the terms "treatment" and "therapy" are defined as the application or administration of a therapeutic agent to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease. Methods and uses of the compositions described herein include treatment methods, which result in any therapeutic or beneficial effect. In particular aspects of the methods and uses of the compositions disclosed herein, expression of the nucleic acid provides a therapeutic benefit to the mammal (e.g., human suffering from DMD). In various embodiments, further included are inhibiting, decreasing or reducing one or more adverse (e.g., physical) symptoms, disorders, illnesses, diseases or complications caused by or associated with a disease (e.g., cardiomyopathy associated with DMD).

By the phrases "therapeutically effective amount" and "effective dosage" is meant an amount sufficient to produce a therapeutically (e.g., clinically) desirable result; for example, the result can be decreasing SLN expression or activity in a cell, preventing or treating DMD in a subject (e.g., mammals including humans), increasing cardiac function in a subject suffering from DMD, etc.

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity can be measured using any appropriate sequence analysis software.

When referring to mutations in a nucleic acid molecule, "silent" changes are those that substitute one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with another amino acid having similar characteristics.

Although compositions, vectors, viruses, kits, and methods similar or equivalent to those described herein can be used in the practice or testing of the present invention, suitable compositions, vectors, viruses, kits, and methods are described below. All publications, patent applications, patents and other references such as GenBank citations and ATCC citations mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1 shows SLN upregulation in the ventricles of DMD models. 1(a): Representative Western blots (uncropped) showing SLN upregulation in the ventricles of mdx and mdx:utr−/− mice. SERCA2a and PLN levels are unchanged. 1(b): Quantitation show that SLN levels are significantly higher in the ventricles of mdx:utr−/− mice compared to that of mdx mice. Data are presented as mean±SEM. The n number for each group and the p values (t-test with Welch's correction) are shown within the graph. 1(c): The rate of $Ca^{2+}$ dependent SR $Ca^{2+}$ uptake and (d) the $V_{max}$ of $Ca^{2+}$ uptake are significantly reduced in the ventricles of both mdx and mdx:utr−/− mice. 1(e): The $EC_{50}$ of $Ca^{2+}$ uptake is unaltered between WT and DMD mice. Data are presented as mean±SEM. The n number for each group and the p values (t-test with Welch's correction) are shown within the graph. Tissues from 3-4 month old mice are used for all the above experiments.

FIG. 2 shows SLN upregulation in muscles of DMD dogs. 2(a): Representative Western blots showing the protein levels of SLN and SERCA isoforms in the ECU muscles of DMD and non-DMD dogs. Uncropped scans of the Western blots are shown in FIG. 15a. 2(b): Quantitation show that SLN and SERCA1 levels are significantly increased, whereas SERCA2a level is significantly decreased in the ECU of DMD dogs. Data are presented as mean±SEM. The n number for each group and the p values (t-test with Welch's correction) are shown within the graph. 2(c): The rate of $Ca^{2+}$ dependent SR $Ca^{2+}$ uptake, and (d) the $V_{max}$ of $Ca^{2+}$ uptake are significantly reduced in the ECU muscles of DMD dogs. 2(e): The $EC_{50}$ of $Ca^{2+}$ uptake is unaltered between non-DMD and DMD dog tissues. Data are presented as mean±SEM. The n number for each group and the p values (t-test with Welch's correction) are shown within the graph.

FIG. 3 shows SLN upregulation in the heart and muscles of DMD patients. 3(a): Western blot analysis of SLN, SERCA1, SERCA2a and CSQ protein levels in the quadriceps of DMD patients. 3(b): Quantitation shows that SLN is upregulated ~1.5 fold and SERCA2a is downregulated >50% in the quadriceps of DMD patients compared to that of non-DMD controls, n=2 per group. 3(c): Western blot analysis of SLN, SERCA2a, PLN and CSQ proteins in the human ventricular biopsies. 3(d): Quantitation show that SLN levels are abnormally high in the ventricular biopsies from DMD patients, n=2 per group. Data are presented as mean±SEM. Uncropped scans of the Western blots are shown in FIG. 15b-15c.

FIG. 12 shows AAV9.shSLN treatment mitigates DMD in mice and decreased mononuclear infiltration in AAV treated groups. 12(a), 12(b): Quantitation of signals from Western blots show that AAV treatment significantly reduced SLN protein expression in both skeletal (pectorals) and ventricles of mdx:utr−/− mice. In addition, AAV treatment suppresses the induction of SERCA2a and CSQ expression in the pectorals of mdx:utr−/− mice. Data are presented as mean±SEM. *significantly different from other groups (n=4 per group, $p<0.05$, t-test with Welch's correction). 12(c): Representative H&E staining of quadriceps and ventricular sections show decreased mononuclear infiltration in AAV treated groups. Original magnification is 5×. Inset is 40× focusing the necrotic areas. Arrow indicates the necrotic areas with mononuclear infiltration. Scale bar is 100 μm.

FIG. 2a; 15(b)

DETAILED DESCRIPTION

Figure 4A:
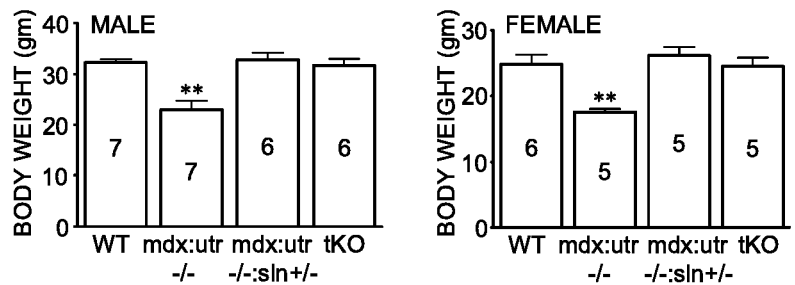
FIG. 4 shows that reduction in SLN expression prolongs the lifespan of mdx:utr−/− mice. 4(a): The body weight of mdx:utr−/−:sln+/− and tKO mice in comparison to that of age- and sex-matched WT and mdx:utr−/− control mice. 3-4 month old mice were used for this experiment. The n number for each group is shown within the bar. Data are presented as mean±SEM. significantly (p<0.005, t-test with Welch's correction) different from other groups. 4(b): Kaplan-Meier survival curves indicate that the mdx:utr−/−:sln+/− and tKO mice has increased lifespan in comparison to that of mdx:utr−/− controls as determined by the nonparametric log-rank test; p<0.0001. 4(c): Increased $Ca^{2+}$ dependent SR $Ca^{2+}$ uptake; 4(d): increased $V_{max}$ of $Ca^{2+}$ uptake; and 4(e): decreased $EC_{50}$ values in the diaphragm of mdx:utr−/−:sln+/− and tKO mice indicates improved SERCA function. The n number for each group is shown within the bar. Data are presented as mean±SEM. significantly (p<0.0005, t-test with Welch's correction) different from other groups. *significantly (p<0.005, t-test with Welch's correction) different from WT and mdx:utr−/− mice. 4(f), 4(g), and 4(h): Representative Western blot analysis and quantitation of SLN, SERCA1, SERCA2a and CSQ proteins in the diaphragm, pectoral and quadriceps muscles respectively. Tissues are from 3-4 month old mice. Uncropped scans of Western blots are shown in FIGS. 14(a) 14(b), and 14(c). Data are represented as mean±SEM. The n number for each group is shown within the bar diagram. *significantly different from other groups, p<0.05, t-test with Welch's correction.
FIG. 4(f); 14(b)
FIG. 4(g); 14(c)
FIG. 4(h); 14(d)

Described herein are compositions, vectors, viruses, and kits including a therapeutically effective amount of an inhibitor of SLN for decreasing SLN expression in a cell, and preventing and treating DMD and in some embodiments, also cardiomyopathy, in a subject (e.g., human). Methods of using these compositions, vectors, viruses, and kits including these compositions, vectors, and viruses are also described herein. The experimental results described herein demonstrate the therapeutic utility of an inhibitor of SLN expression for reducing SLN expression, attenuating muscle pathology, improving the diaphragm, skeletal muscle and cardiac function, and extending life span. The experimental results described herein also demonstrate the therapeutic utility of inhibiting SLN expression for preventing DMD in a subject. These compositions, vectors and kits are novel therapies for DMD and associated cardiomyopathy.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; The Condensed Protocols From Molecular Cloning: A Laboratory Manual, by Joseph Sambrook et al., Cold Spring Harbor Laboratory Press, Cold Spring Harbor, N.Y., 2006; and Current Protocols in Molecular Biology, ed. Ausubel et al., Greene Publishing and Wiley-Interscience, New York, 1995 (with periodic updates). Conventional methods of gene transfer and gene therapy may also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; Viral Vectors for Gene Therapy: Methods and Protocols, ed. Otto-Wilhelm Merten and Mohammed Al-Rubeai, Humana Press, 2011; and Nonviral Vectors for Gene Therapy: Methods and Protocols, ed. Mark A. Findeis, Humana Press, 2010. Methods for constructing and using viral vectors are known in the art (see, e.g., Miller and Rosman, BioTechniques 1992, 7:980-990). Methods for large-scale production of rAAV are described in Urabe M. J. (2006) Virol. 80:1874-1885; Kotin R. M. (2011) Hum. Mol. Genet. 20:R2-6; Kohlbrenner E. et al. (2005) Mol. Ther. 12:1217-1225; and Mietzsch M. (2014) Hum. Gene Ther. 25:212-222. For a review of rAAV gene therapy methods, see Samulski, R. J. and Muzyczka, N. (2014) AAV-Mediated Gene Therapy for Research and Therapeutic Purposes, Annu. Rev. Virol. 1:427-451. rAAV vectors, variants, chimeras, and rAAV vector mediated gene transfer methods are described in U.S. Pat. No. 9,840,719.

Compositions and Vectors for Reducing SLN Expression and Activity and Preventing and Treating DMD and Associated Cardiomyopathy Compositions described herein for reducing SLN expression and/or activity include a therapeutically effective amount of an inhibitor of SLN. In some embodiments, a therapeutically effective amount is an amount effective for improving SERCA function in dystrophic muscles in a subject. The compositions can also include a pharmaceutically acceptable carrier. Reducing SLN expression includes reducing SLN transcription and inhibiting processing of SLN RNAs. Reducing SLN activity includes reducing the inhibitory effect of SLN, reducing SLN interaction with SERCA and preventing SLN to go to the membrane. Any therapeutic molecule that reduces SLN expression and/or activity may be used including an RNA molecule. Examples of RNA molecules include interfering RNA molecules such as shRNA, RNAi, and microRNA (miRNA).

If an interfering RNA is used as the inhibitor of SLN, the interfering RNA is typically contained with an expression vector or a viral vector. The vectors may be episomal, e.g., plasmids, virus-derived vectors, or may be integrated into the target cell genome, through homologous recombination or random integration. Any suitable expression vector (e.g., viral vector) can be used. Viruses are naturally evolved vehicles which efficiently deliver their genes into host cells and therefore are desirable vector systems for the delivery of therapeutic nucleic acids. Preferred viral vectors exhibit low toxicity to the host cell and produce/deliver therapeutic quantities of the nucleic acid of interest (in some embodiments, in a tissue-specific manner). A number of viral based systems have been developed for gene transfer into mammalian cells. For example, AAV provide a convenient platform for gene delivery systems. As another example, retroviruses provide a convenient platform for gene delivery systems. In yet other examples, adenovirus vectors, retrovirus vectors, herpesvirus vectors, alphavirus vectors, or lentivirus vectors are used. A selected nucleic acid sequence can be inserted into a vector (a vector genome) and packaged in viral particles using techniques known in the art (e.g., an rAAV vector packaged in rAAV particles). The recombinant virus can then be isolated and delivered to cells of the subject.

In the experiments described herein, SLN expression was reduced using shRNA specific for SLN, and in these experiments, a nucleic acid sequence encoding the shRNA specific for SLN was contained within a rAAV (serotype 9) vector. Any suitable rAAV vector can be used. Recombinant AAV vectors include AAV1, AAV2, AAV3, AAV4, AAV5, AAV6, AAV7, AAV8, AAV9, AAV10, AAV11, Rh10, Rh74 or AAV-2i8, and variants thereof. Examples of rAAV can include capsid sequence of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Particular capsid variants include capsid variants of AAV1, AAV2, AAV3, AAV4, AAV5, AAV6, AAV7, AAV8, AAV9, AAV10, AAV11, Rh10, Rh74 or AAV-2i8, such as a capsid sequence with an amino acid substitution, deletion or insertion/addition. AAV vectors can include additional elements that function in cis or in trans. In particular embodiments, an rAAV vector that includes a vector genome also has: one or more inverted terminal repeat (ITR) sequences that flank the 5' or 3' terminus of the nucleic acid sequence encoding shRNA specific for SLN; an expression control element that drives transcription (e.g., a promoter or enhancer) of the nucleic acid sequence, such as a constitutive or regulatable control element, or tissue-specific expression control element; and/or a poly-Adenine sequence located 3' of the nucleic acid sequence.

In a typical embodiment, an AAV serotype having muscle tropism is used. For example, in humans, AAV2 and AAV9 have high muscle tropism (for reviews of in vivo tissue tropisms, see Nonnenmacher M. and Weber T. (2012) Gene Ther. 19:649-658; Agbandje-McKenna M. and Kleinschmidt J. (2011) AAV capsid and cell interactions—In Adeno-Associated Virus: Methods and Protocols, ed. R O Snyder, P Moullier, p. 47-92, Humana Press, Clifton, N.J.; and Asokan A. et al. (2012) Mol. Ther. 4:699-708). In some embodiments, rAAV8 can be used.

Methods are well known in the art for generating rAAV vectors and rAAV (virions) having improved features for delivering therapeutic agents. rAAV having new capsid variants that, for example, have higher transduction frequency or increased muscle tropism, can be used. For example, capsid libraries can be screened in a process called directed evolution (Bartel M. A. (2012) Gene Ther. 19:694-700) to select capsids enriched for infecting a particular tissue or cell type. As another example, rAAV having capsids decorated with ligand targeted to a specific cell type (e.g., cardiac muscle-specific) can be used. As another example, pseudotyped rAAV (nucleic acid or genome derived from a first AAV serotype that is encapsidated or packaged by an AAV capsid containing at least one AAV Cap protein of a second serotype (i.e., one different from the first AAV serotype)) can be used. In addition to capsid modifications, rAAV as described herein may include tissue-specific promoters (e.g., muscle-specific promoters) and inducible promoters. For a review of rAAV gene therapy methods, see Samulski, R. J. and Muzyczka, N. (2014) AAV-Mediated Gene Therapy for Research and Therapeutic Purposes, Annu. Rev. Virol. 1:427-451. rAAV, variants, chimeras, and rAAV-mediated gene transfer methods are also described in U.S. Pat. No. 9,840,719.

rAAV can be produced using any suitable methods. Methods for large-scale production of rAAV are known and are described in Urabe M. J. (2006) Virol. 80:1874-1885; Kotin R. M. (2011) Hum. Mol. Genet. 20:R2-6; Kohlbrenner E. et al. (2005) Mol. Ther. 12:1217-1225; Mietzsch M. (2014)

Hum. Gene Ther. 25:212-222; and U.S. Pat. Nos. 6,436,392, 7,241,447, and 8,236,557. For example, the Bac-to-Bac System (Invitrogen) can be used. For the experiments described herein, plasmid pFB-ITR-sh-SLN was used to create a recombinant baculovirus using the Bac-to-Bac system (Invitrogen). The AAV9.shSLN was produced in Sf9 insect cells and purified mostly as previously described in Urabe M. et al. (2002) Human Gene Ther 13:1935-1942 (with the exception that BacCap9 was used instead of BacVP). In this method, virus was purified by iodixanol gradient ultracentrifugation and dialyzed into Lactated Ringer's solution.

The vectors described herein typically include one or more expression control elements. Expression control elements include ubiquitous or promiscuous promoters/enhancers which are capable of driving expression of a polynucleotide (nucleic acid) in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature, the SV40 promoter, the dihydrofolate reductase (DHFR) promoter, the cytoplasmic β-actin promoter, the phosphoglycerol kinase (PGK) promoter, etc.

Expression control elements include those active in a particular tissue or cell type, referred to herein as a "tissue-specific expression control elements/promoters." Tissue-specific expression control elements are typically active in a specific cell or tissue (e.g., muscle). Expression control elements also can confer expression in a manner that is regulatable, that is, a signal or stimuli increases or decreases expression of the operably linked nucleic acid. A regulatable element that increases expression of the operably linked nucleic acid in response to a signal or stimuli is also referred to as an "inducible element" (i.e., is induced by a signal). A regulatable element that decreases expression of the operably linked nucleic acid in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

Expression control elements also include native elements(s). A native control element (e.g., promoter) may be used when it is desired that expression of the nucleic acid may mimic the native expression. A native element may be used when expression of the nucleic acid is to be regulated temporally or developmentally, or in a tissue-specific manner, or in response to specific transcriptional stimuli. Other native expression control elements, such as introns, polyadenylation sites or Kozak consensus sequences may also be used.

Any suitable non-viral delivery methods can also be used. Non-viral mediated delivery of ShRNA or siRNA for SLN can be achieved, for example, through binding of siRNA or shRNA to natural or synthetic polymers such as, for example, PEI, poly-1-lysin and dendrimers. These polymers protect the siRNA from nuclease attack and enhance the update of siRNA to the system.

In some embodiments, a composition for preventing or treating DMD, and in some embodiments cardiomyopathy, can include an inhibitor of SLN and a known DMD therapeutic. For example, such a composition can include an interfering RNA molecule specific for SLN (e.g., shRNA specific for SLN) and a known DMD therapeutic. Examples of known DMD therapeutics include but are not limited to eteplirsen, and micro-dystrophin (μ-dys). In some embodiments, a combined gene therapy can be used, in which a nucleic acid that decreases SLN expression is combined with a nucleic acid encoding μ-dys. For example, a composition for DMD prevention or treatment can include both a AAV9.shSLN and a viral vector expressing μ-dys (e.g., AAV9μdys).

Methods for Reducing SLN Expression and Activity and Preventing and Treating DMD and Associated Cardiomyopathy in a Subject Described herein are methods for reducing SLN expression or activity in a cell. These methods include contacting a cell with a vector, virus, or composition as described herein. Also described herein are methods of preventing and treating DMD in a subject, and in some embodiments, also associated cardiomyopathy in the subject. Typically, the compositions, vectors, and viruses are delivered to appropriate target cells in the subject (e.g., human patient). A typical target cell is any muscle cell that has elevated (upregulated) levels of SLN.

The methods include administration of any of the compositions, vectors and viruses described herein. Administration of a composition, vector or virus as described herein to the subject results in prevention, amelioration, or treatment of DMD (e.g., prevention, alleviation or mitigation of DMD symptoms or pathology) in a subject, and in some embodiments, additionally associated cardiomyopathy (e.g., prevention, alleviation or mitigation of cardiomyopathy symptoms or pathology). In a typical embodiment, administration of a composition, virus or vector to a subject having DMD reduces SLN expression, restores SERCA function, improves LV systolic function and cardiac remodeling, improves forelimb muscle strength, and extends life span. In an embodiment for preventing DMD in a subject who is predisposed to having DMD, a composition, virus or vector is administered to the subject having a mutation(s) in the dystrophin gene. SLN upregulation in myoblasts (a primordial muscle cell) from DMD models suggests that SLN upregulation is an intrinsic feature in dystrophin deficient/mutant muscle cells. Hence, administration of a composition, virus or vector to reduce SLN expression can be performed as soon as the mutation is identified even before the symptoms appear. Administration or in vivo delivery to a subject can be performed prior to development of an adverse symptom, condition, complication, etc.

As described above, combination therapies may be used to prevent or treat DMD and associated cardiomyopathy in a subject. In some embodiments, a combination therapy involves administering a nucleic acid sequence encoding shRNA specific for SLN and a known DMD therapeutic. In one example of such an embodiment, a first AAV9.shSLN is administered to the subject and a second virus including a second viral vector expressing μ-dys (e.g., AAV9μdys) is administered to the subject. In such an embodiment, the two viruses can be administered in the same composition simultaneously, or they can be administered at different time points (e.g., two different compositions administered at two different time points). In another example of a combination therapy, a AAV9.shSLN is administered to the subject in combination with another DMD therapeutic such as a drug (e.g., a DMD drug such as eteplirsen). In any combination therapy, the two or more therapeutics can be administered simultaneously, concurrently or sequentially, e.g., at two or more different time points. Typically, such a combination therapy restores dystrophin function and improves SERCA function and mitigates both skeletal and cardiac muscle pathology. In one embodiment of combination therapy, a composition that reduces SLN expression and a composition that increases μ-dys levels or expression are admixed in the same injection or infusion volume.

Any suitable methods of administering such a composition, virus or vector to a subject may be used. In these methods, the compositions, viruses and vectors can be administered to a subject by any suitable route, e.g., intramuscularly, systemically by intravenous injection, orally, via intranasal delivery, etc. The compositions may be administered by catheter to a site accessible by a blood vessel.

In some embodiments, rAAV including a nucleic acid sequence encoding shRNA specific for SLN are administered to a subject via a bolus injection into artery or portal vein. If administered via intravenous injection, the compositions may be administered in a single bolus, multiple injections, or by continuous infusion (e.g., intravenously, by peritoneal dialysis, pump infusion). In other embodiments, rAAV including a nucleic acid sequence encoding shRNA specific for SLN are administered to a subject via limb infusion in muscle (Sun B. et al. (2010) Gene Ther. 17:1500-1505). For parenteral administration, the compositions are preferably formulated in a sterilized pyrogen-free form. As indicated above, the compositions described herein may be in a form suitable for sterile injection. To prepare such a composition, the suitable active therapeutic(s) (e.g., a shRNA specific for SLN, a vector encoding same, a recombinant virus) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the therapeutics is only sparingly or slightly soluble in water, a dissolution enhancing or solubilizing agent can be added, or the solvent may include 10-60% w/w of propylene glycol or the like. The compositions, viruses and viral vectors described herein may be administered to mammals (e.g., rodents, humans, nonhuman primates, canines, felines, ovines, bovines) in any suitable formulation according to conventional pharmaceutical practice (see, e.g., Remington: The Science and Practice of Pharmacy (20th ed.), ed. A. R. Gennaro, Lippincott Williams & Wilkins, (2000) and Encyclopedia of Pharmaceutical Technology, eds. J. Swarbrick and J. C. Boylan, Marcel Dekker, New York (1988-1999), a standard text in this field, and in USP/NF). A description of exemplary pharmaceutically acceptable carriers and diluents, as well as pharmaceutical formulations, can be found in Remington: supra. Other substances may be added to the compositions to stabilize and/or preserve the compositions. As used herein the terms "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a viral vector or viral particle to a subject.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Viral vectors (e.g., AAV vectors), viruses and pharmaceutical compositions thereof, can be packaged in single or multiple unit dosage form for ease of administration and uniformity of dosage.

The therapeutic methods described herein in general include administration of a therapeutically effective amount of the compositions or vectors described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof (e.g., DMD, cardiomyopathy). Determination of those subjects "at risk" can be made by any objective or subjective determination by a diagnostic test or opinion of a subject or health care provider.

Additional Embodiments

The compositions, vectors, viruses and methods described herein can be used to decrease SLN expression in any tissue where SLN is elevated. For example, because SLN is also elevated in the ventricles of patients with mitral regurgitation, and in patients with Tako-Tsubo cardiomyopathy, and in the muscles of Emery-Dreifuss muscular dystrophy, SLN can be targeted in these diseases and SLN expression could be decreased by administering the compositions, viruses and vectors described herein.

Effective Doses

The compositions, viruses and vectors described herein are preferably administered to a mammal (e.g., human) in an effective amount, that is, an amount capable of producing a desirable result in a treated mammal (e.g., reducing SLN expression, restoring SERCA function, improving LV systolic function and cardiac remodeling, improving forelimb muscle strength, extending life span). Such a therapeutically effective amount can be determined according to standard methods. Toxicity and therapeutic efficacy of the compositions and vectors utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. A delivery dose of a composition, virus or vector as described herein is determined based on preclinical efficacy and safety.

Kits

Described herein are kits for inhibiting SLN expression or activity, and preventing and treating DMD and associated cardiomyopathy in a subject. A typical kit includes a composition including a pharmaceutically acceptable carrier (e.g., a physiological buffer) and a therapeutically effective amount of an inhibitor of SLN (e.g., shRNA specific for SLN); and instructions for use. In some embodiments, a kit will also include a known DMD therapeutic (e.g., a kit containing a first vector encoding shRNA specific for SLN and a second vector encoding μDys, or recombinant viruses including viral vectors). Such a kit can be used for combination therapy. Kits also typically include a container and packaging. Instructional materials for preparation and use of the compositions and vectors described herein are generally included. While the instructional materials typically include written or printed materials, they are not limited to such. Any medium capable of storing such instructions and communicating them to an end user is encompassed by the kits herein. Such media include, but are not limited to electronic storage media (e.g., magnetic discs, tapes, cartridges, chips), optical media (e.g., CD ROM), and the like. Such media may include addresses to internet sites that provide such instructional materials.

Data and Analysis

Use of the compositions, viruses, vectors, kits and methods described herein may employ conventional biology methods, software and systems. Useful computer software products typically include computer readable medium having computer-executable instructions for performing logic steps of a method. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The compositions, viruses, vectors, kits and methods described herein may also make use of various computer program products and software for a variety of purposes, such as reagent design, management of data, and analysis. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Additionally, the embodiments described herein include methods for providing data (e.g., experimental results, analyses) and other types of information over networks such as the Internet.

EXAMPLES

The present invention is further illustrated by the following specific examples. The examples are provided for illustration only and should not be construed as limiting the scope of the invention in any way.

Example 1

Reducing Sarcolipin Expression Mitigates DMD and Associated Cardiomyopathy in Mice Here it is shown that reducing SLN levels ameliorates dystrophic pathology in the severe dystrophin/utrophin double mutant (mdx:utr−/−) mouse model of DMD. Germline inactivation of one-allele of the SLN gene normalizes SLN expression, restores SERCA function, mitigates skeletal muscle and cardiac pathology, improves muscle regeneration, and extends the lifespan. To translate these findings into a therapeutic strategy, SLN expression was knocked down in one-month old mdx:utr−/− mice AAV9-mediated RNA interference. The AAV treatment markedly reduced SLN expression, attenuated muscle pathology and improved diaphragm, skeletal muscle and cardiac function. Taken together, these findings show that SLN reduction is a therapeutic approach for DMD.

To determine whether SLN upregulation is a common molecular change in skeletal muscles and in the heart in DMD, SLN protein levels were analyzed in the ventricles of DMD mice. Results show that SLN levels were abnormally high in the ventricles of both mdx and mdx:utr−/− mice. Furthermore, SLN levels were ~2 fold higher in the ventricles of mdx:utr−/− mice compared to that of mdx mice (FIG. 1a-1b). The expression levels of SERCA2a and phospholamban (PLN) were unaltered in the dystrophic hearts. However, the rate of $Ca^{2+}$ dependent $Ca^{2+}$ uptake (FIG. 1c) and the maximum velocity ($V_{max}$) of $Ca^{2+}$ uptake (FIG. 1d) were significantly reduced; whereas the $EC_{50}$ of $Ca^{2+}$ uptake was unaltered in the ventricles of DMD mice (FIG. 1e). Similar changes were observed in the skeletal muscle of the canine DMD model. SLN protein expression was significantly increased in the extensor carpi ulnaris (ECU) muscles of affected dogs compared to that of non-DMD controls (FIG. 2a-2b). Further, SERCA 1 levels were significantly increased and SERCA2a levels were decreased in these muscles (FIG. 2a-2b). Regardless of the changes in SERCA isoforms, the rate of $Ca^{2+}$ dependent $Ca^{2+}$ uptake (FIG. 2c) and the $V_{max\ of}$ $Ca^{2+}$ uptake (FIG. 2d) were significantly reduced in dystrophic dog muscles. The $EC_{50}$ for $Ca^{2+}$ activation was not significantly different between the non-DMD and DMD dog tissues (FIG. 2e) indicating the $Ca^{2+}$ affinity of the SERCA pump was not altered. Similar to animal models, SLN levels were increased both in the quadriceps (FIG. 3a-3b) and in the ventricles (FIG. 3c-3d) of DMD patients. These findings revealed SLN upregulation as a common molecular change in dystrophin-deficient skeletal and cardiac muscles of both DMD patients and DMD models.

Figure 4B:
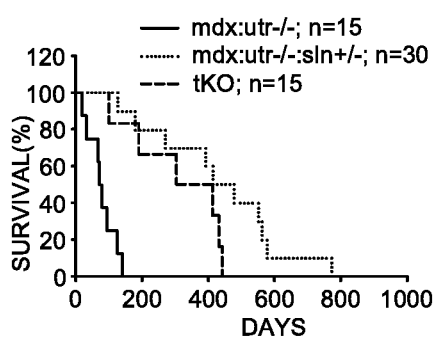

Ablation of SLN extends the lifespan of mdx:utr−/− mice. To determine the role of SLN upregulation in DMD, SLN haploinsufficient mdx:utr−/− knockout (mdx:utr−/−:sln+/−) and SLN deficient mdx:utr−/− (mdx:utr−/−:sln−/−) triple knockout (tKO) mice were generated. The mdx:utr−/−: sln+/− and tKO pups were delivered normally. The body weight of mdx:utr−/−:sln+/− and tKO mice were normalized (FIG. 4a) and their lifespan was significantly extended (FIG. 4b; p<0.0001 by the nonparametric log-rank test). The median survival was increased by 446 and 358 days, respectively for mdx:utr−/−:sln+/− and tKO mice compared to that of mdx:utr−/− littermates (73 days). These findings suggest that SLN reduction or ablation markedly improves survival to mdx:utr−/− mice.

Figure 4C:
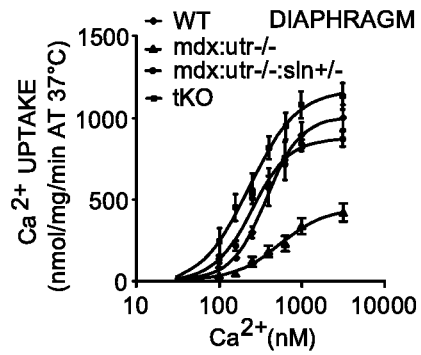
Figure 4D:
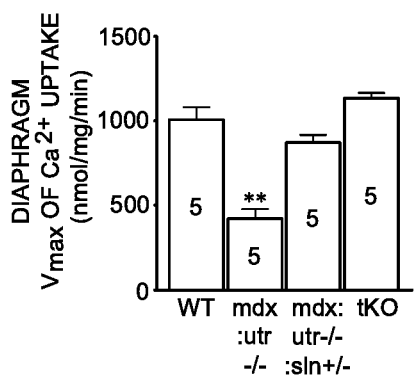
Figure 4E:
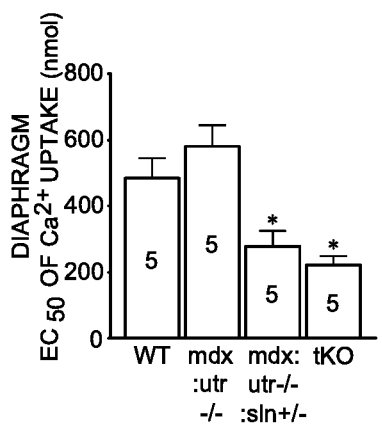

Reducing SLN expression restores SERCA function in DMD. Deletion of one allele of the SLN gene improved the rate (FIG. 4c) and $V_{max}$ (FIG. 4d) of SR $Ca^{2+}$ uptake in the diaphragm of mdx:utr−/−mice close to that of WT mice. Complete loss of SLN resulted in a further increase in the rate of $Ca^{2+}$ uptake in the tKO diaphragm; however, the $V_{max}$ of $Ca^{2+}$ uptake was not statistically different from the WT controls (FIG. 4d). Furthermore, the $EC_{50}$ for $Ca^{2+}$ activation was significantly decreased in the diaphragm of both mdx:utr−/−:sln+/− and tKO mice (FIG. 4e), indicating an increase in the apparent affinity of SERCA pump for $Ca^{2+}$ ions in SLN deficient dystrophic muscles. Together, these findings suggest that SLN upregulation is the major cause of SERCA dysfunction in dystrophic muscles.

Figures 4F, 4G, 4H:
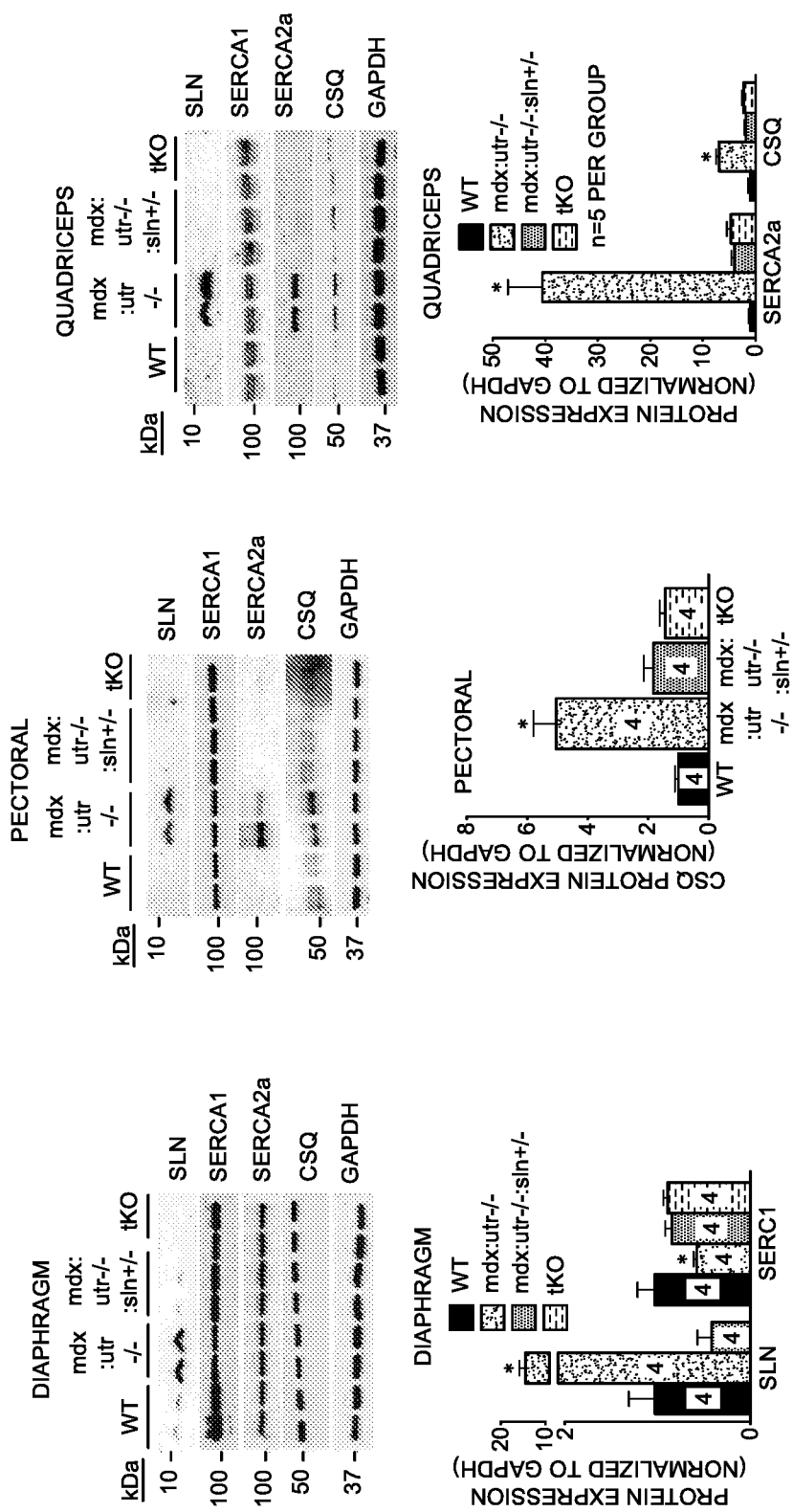

It was determined whether or not SLN ablation affected the expression levels of SERCA isoforms and calsequestrin (CSQ) in dystrophic diaphragm, quadriceps and pectoral muscles. Deletion of one SLN allele reduced the SLN protein expression close to that of WT controls in diaphragm, pectoral and quadriceps muscles (FIG. 4f-4h). Further, the results showed that reduction or ablation of SLN restored the SERCA isoform expression as well as normalized CSQ levels in these muscles (FIG. 4f-4h). Taken together, these findings suggest that SLN haploinsufficiency is sufficient to normalize SLN expression and reinstate SR function in dystrophic muscles.

Figure 5A:
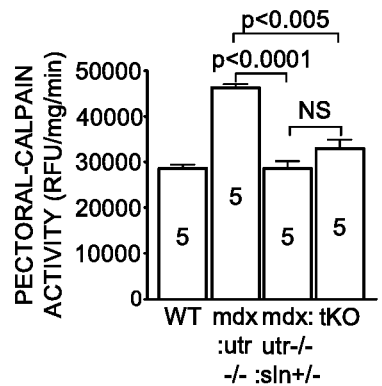
FIG. 5 shows that reduction in SLN expression ameliorates muscle pathology. 5(a): Calpain activity is restored to normal levels in the pectoral muscles of mdx:utr−/−:sln+/− and tKO mice. Data are presented as mean±SEM (t-test with Welch's correction) of five independent experiments performed in duplicates. The n number for each group is shown within the bar. 5(b): Representative H&E and Masson's trichrome-stained quadriceps and diaphragm muscles. Arrow indicates increased mononuclear infiltration (indicative of necrosis) and collagen (blue) accumulation (indicative of fibrosis) in mdx:utr−/− mice. Original magnification is 20×. Scale bar, 100 μm. 5(c), 5(d), 5(e), 5(f): Quantitation show that the necrotic and fibrotic areas were significantly reduced in both diaphragm and quadriceps of mdx:utr−/−:sln+/− mice and in the quadriceps of tKO mice in comparison to that of mdx:utr−/− controls. The n number for each group and the p values (t-test with Welch's correction) are shown within the graph. Data are presented as mean±SEM. Tissues from 3-4 month old mice are used for all the above experiments.
Figure 5C:
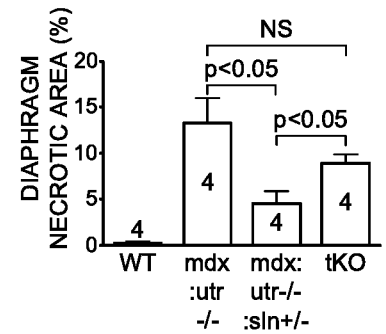
Figure 5D:
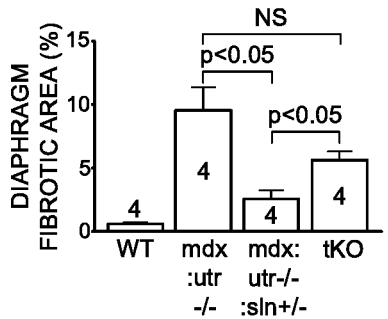
Figure 5E:
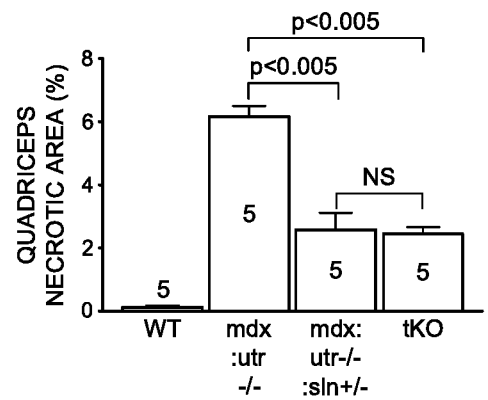
Figure 5F:
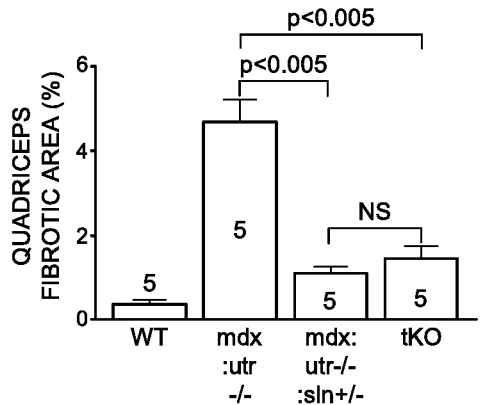
Figure 5B:
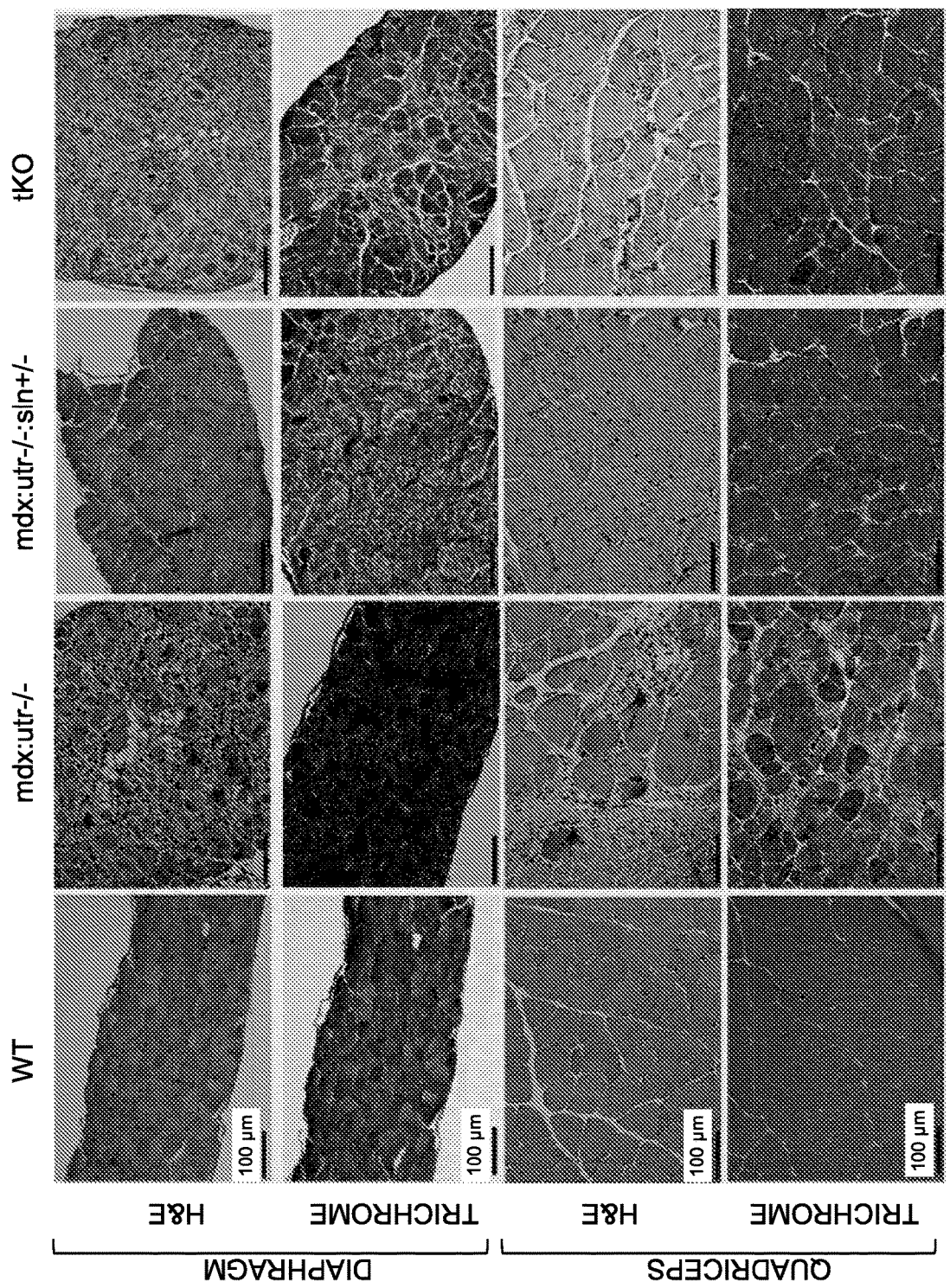
Figure 6A:
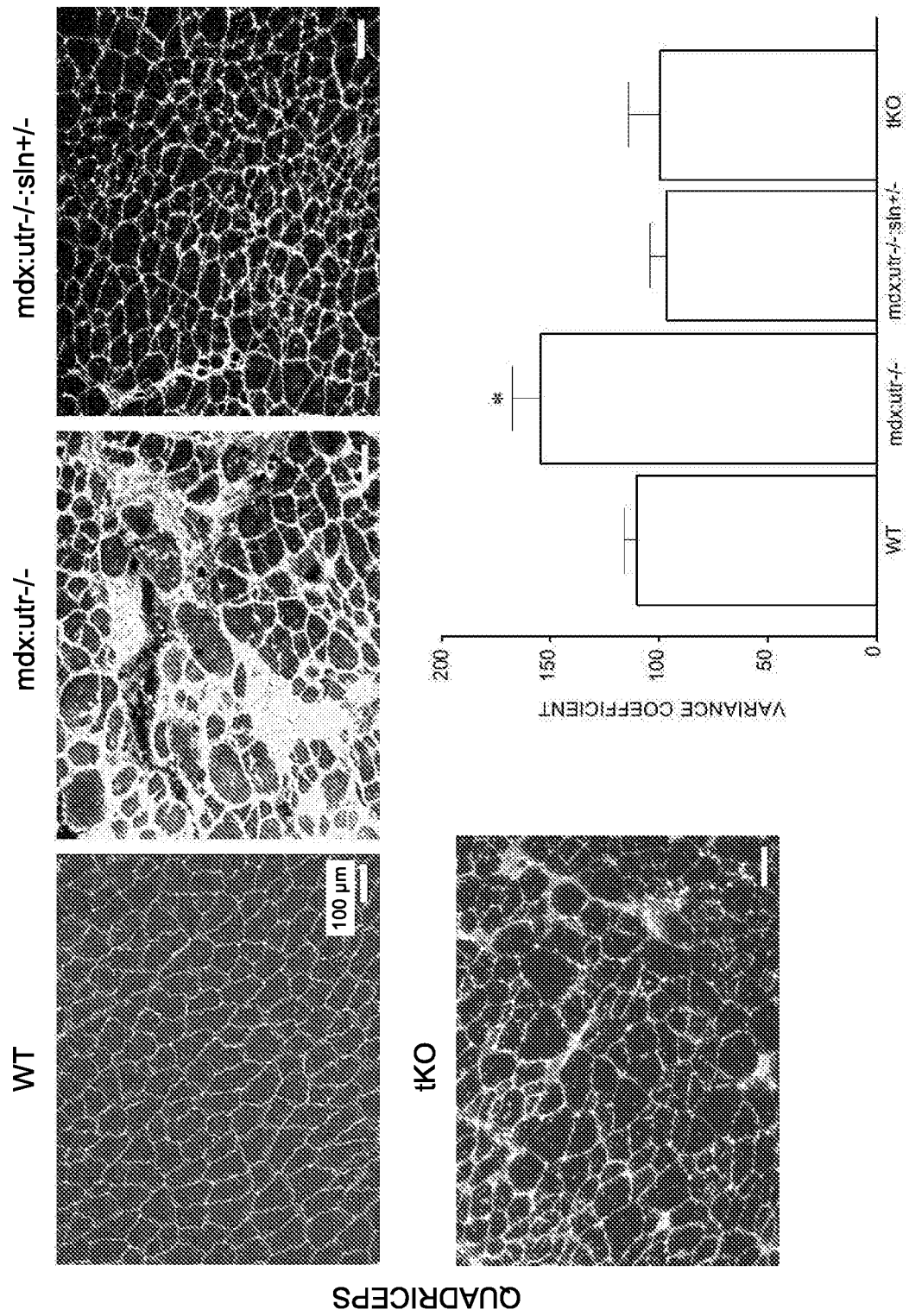
FIGS. 6a; and 15(c)
Figure 6B:
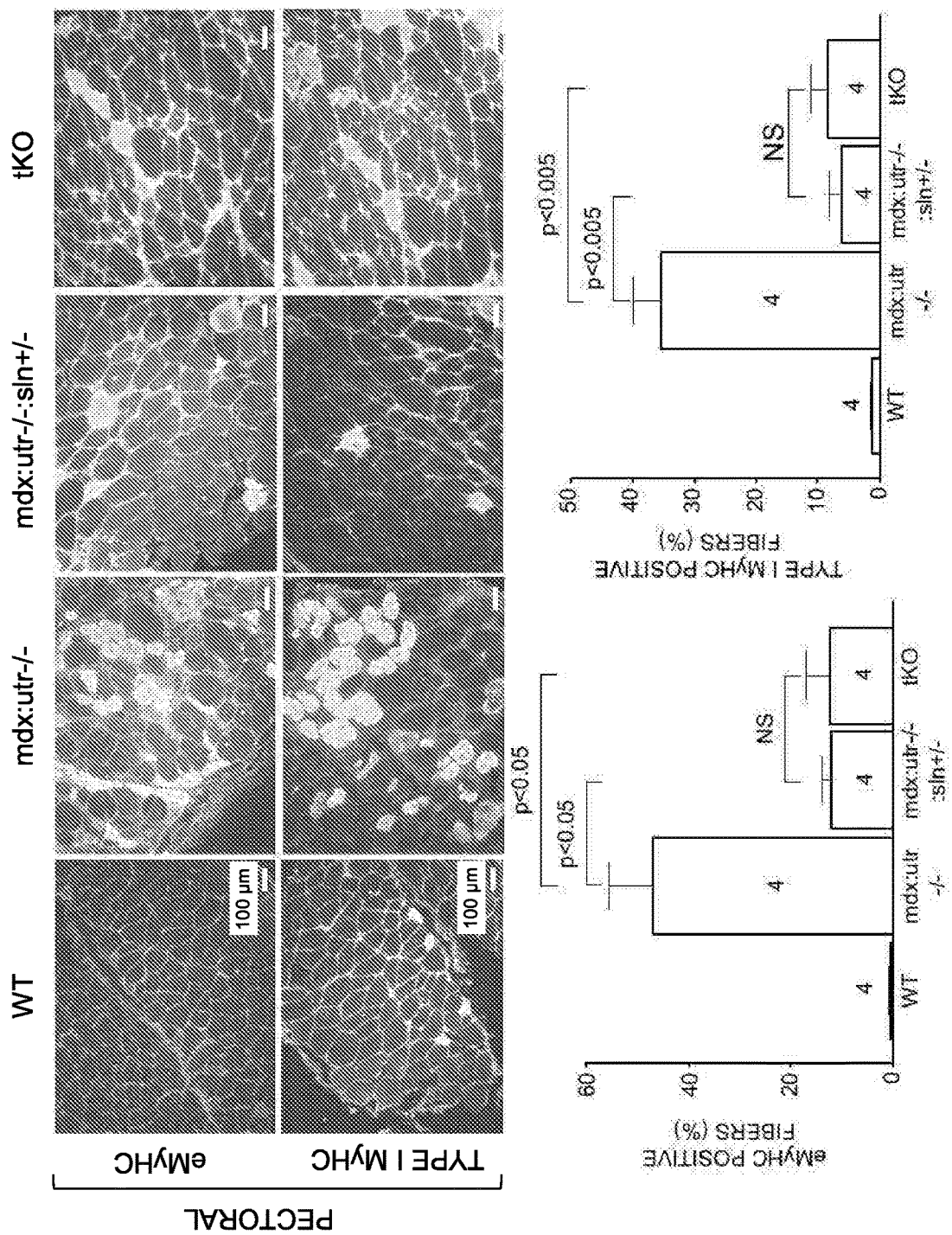
FIG. 6 shows that reduction in SLN expression improves muscle regeneration and prevents fiber-type transition. 6(a): Representative images of WGA stained sections of quadriceps used for fiber size measurements. Original magnification is 10×. The measurements of minimal "Feret's" diameter variance coefficients (VC) of the muscle fiber size shown in the bar graph indicates that VC of fiber size is significantly reduced in the quadriceps of mdx:utr−/−:sln+/− and tKO mice. Data are presented as mean±SEM of four independent experiments. *significantly different from other groups (p<0.05, t-test with Welch's correction). Scale bar, 100 μm. 6(b): Representative images of pectoral muscle sections immunostained for eMyHC or Type I MyHC and stained with WGA. Original magnification is 10×. Scale bar, 100 μm. The quantitation of muscle fibers positive for eMyHC and Type I MyHC are shown in the bar graph. The n number for each group and the p values (t-test with Welch's correction) are shown within the graph. Data are presented as mean±SEM. NS-not statistically significant. Tissues from 3-4 month old mice are used for all the above experiments.
FIG. 6c.

Reducing SLN expression ameliorates muscle pathophysiology. It was next determined whether the improvement in $Ca^{2+}_i$ cycling via enhanced SERCA function reduced the $Ca^{2+}$ dependent protease activity and prevented muscle damage. Reduction or ablation of SLN expression attenuated the calpain activity in pectoral muscle, a representative and severely affected dystrophic muscle (FIG. 5a). Histopathological analysis (FIG. 5b) and quantitation showed significant reduction in necrosis and fibrosis in both diaphragm (FIG. 5c-5d) and quadriceps (FIG. 5e-5f) of mdx:utr−/−:sln+/− mice and in the quadriceps of tKO mice. These improvements were less prominent in the tKO diaphragm and were not statistically different from the mdx:utr−/− controls. Next it was determined if the muscle fiber size in quadriceps by measuring the minimal Feret's diameter variance coefficient (VC) following wheat germ agglutinin (WGA) staining (FIG. 6a). The VC was significantly increased in the muscles of mdx:utr−/− mice indicating heterogeneity in fiber size. On the other hand, in the muscles of mdx:utr−/−:sln+/− and tKO mice, the VC was significantly reduced indicating reduction in small regenerating split fibers and hypertrophic fibers. Next it was determined whether SLN ablation has any effect on the muscle regeneration process as well as fiber-type transition. Immunostaining and quantitation showed that fibers expressing embryonic myosin heavy chain (eMyHC) or Type I MyHC were significantly higher in the pectoral muscles of mdx:utr−/− mice (FIG. 6b) and was consistent with previous findings on the dystrophic quadriceps. In contrast, the number of fibers expressing these proteins were significantly decreased in the muscles of mdx:utr−/−:sln+/− and tKO mice (FIG. 6b). These findings suggest that reduction in SLN expression can improve the muscle regeneration process as well as prevent the fiber-type transition in dystrophic muscles.

Figure 7A:
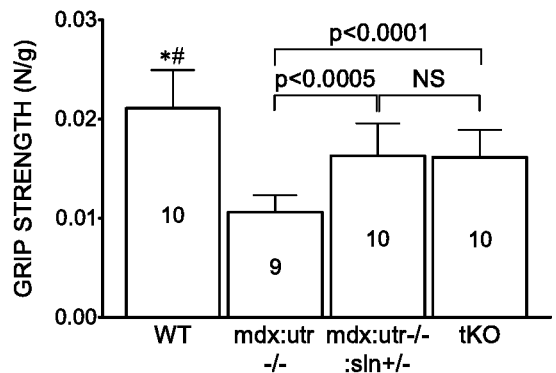
FIG. 7 shows that reduction in SLN expression improves skeletal muscle function in mdx:utr−/− mice. 7(a): Forelimb strength measured using a grip strength meter shows improved muscle strength in the mdx:utr−/−:sln+/− and tKO mice. 3-4 month old male and female mice were used for this study. The n number for each group is shown within the bar. Data are presented as mean±SEM (t-test with Welch's correction). #p<0.0001 vs. mdx:utr−/−. *p<0.05 vs. mdx:utr−/−:sln+/− and tKO mice. 7(b), 7(e): Representative traces of twitch force at 2 Hz for EDL and hemidiaphragm respectively. 7(c), 7(f): The maximum force generated by the EDL and hemidiaphragm at 2 Hz are significantly increased in the mdx:utr−/−:sln+/− mice compared to that of mdx:utr−/− mice. The n number for each group is shown within the bar. Data are presented as mean±SEM. 7(d), 7(g): Force-frequency curves indicating that force generated by EDL and hemidiaphragm in the mdx:utr−/−:sln+/− mice are significantly increased at all frequencies. EDL and hemidiaphragm are from 3-4 month old mice.
Figure 7B:
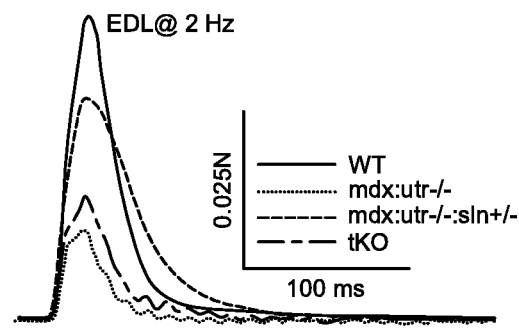
Figure 7C:
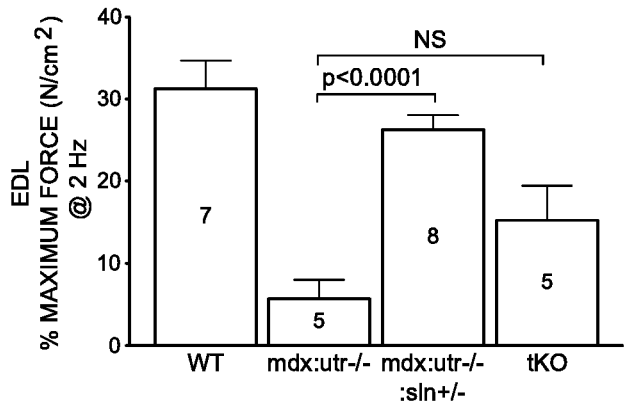
Figure 7D:
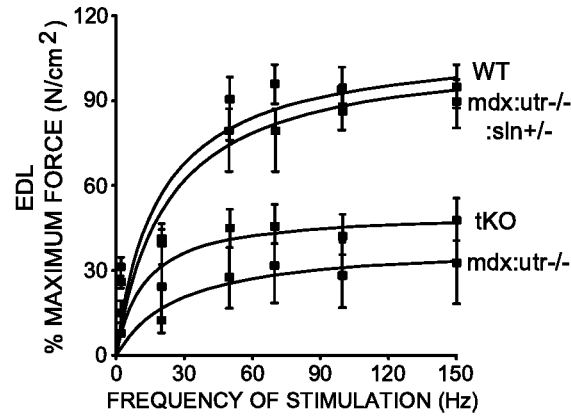
Figure 7E:
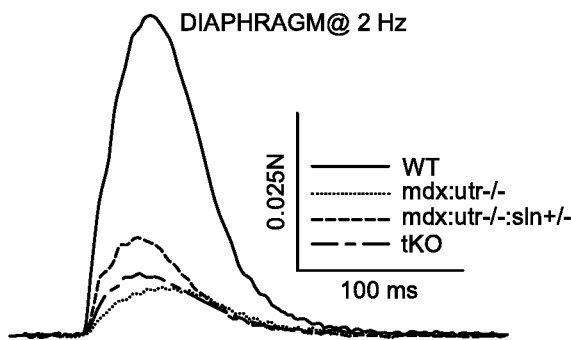
Figure 7F:
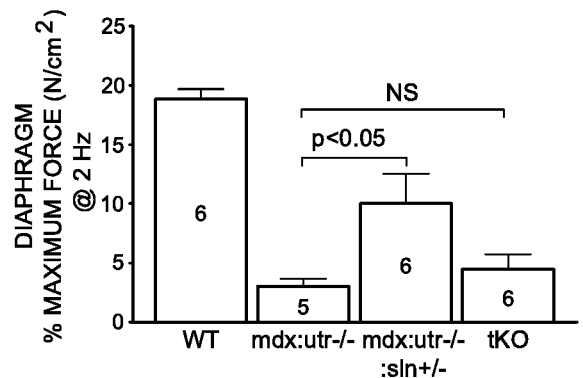
Figure 7G:
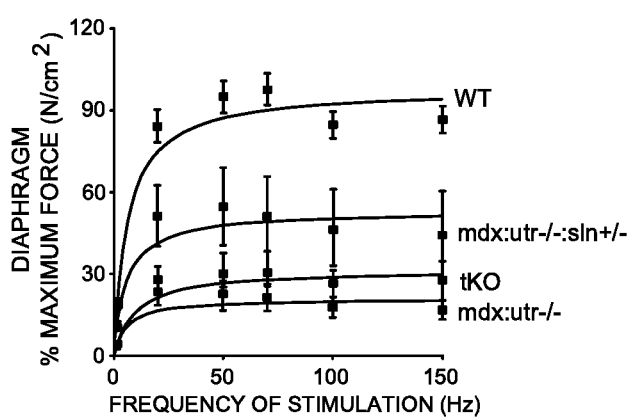
Figure 8A:
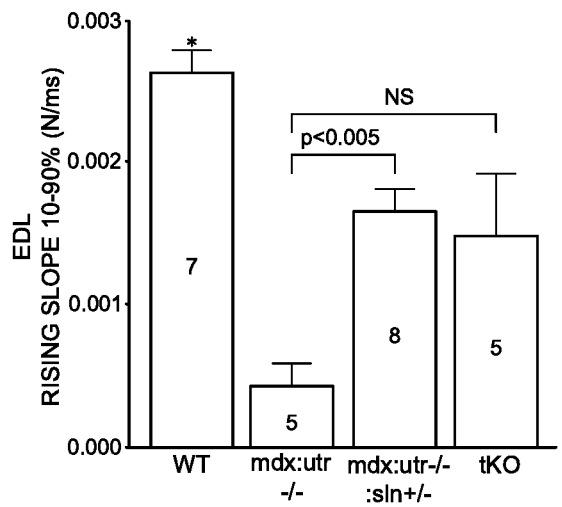
FIG. 8 shows that reduction in SLN expression improves muscle contraction. 8(a), 8(b): The EDL muscles from mdx:utr−/−:sln+/− mice exhibits increased rate of contraction as represented by 10%-90% rising slope and increased rate of relaxation as represented by 90%-10% decay slope at 2 Hz in comparison with that of mdx:utr−/− mice. 8(c), 8(d): These changes were less prominent in the diaphragm of mdx:utr−/−:sln+/− mice. Data are presented as mean±SEM. The n number for each group and the p values (t-test with Welch's correction) are shown within the graph. *significantly different from other groups (p<0.05).
Figure 8B:
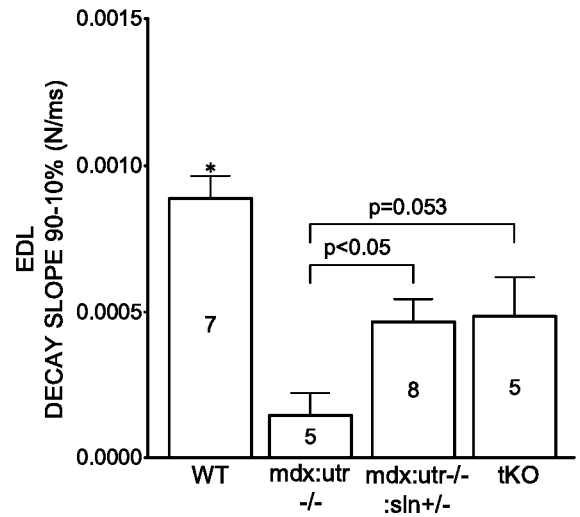
Figure 8C:
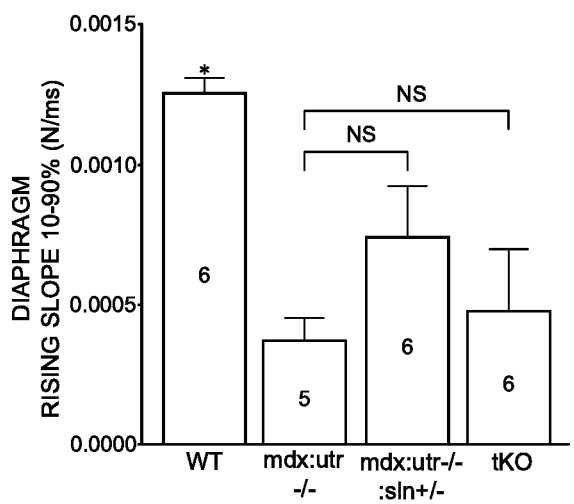
Figure 8D:
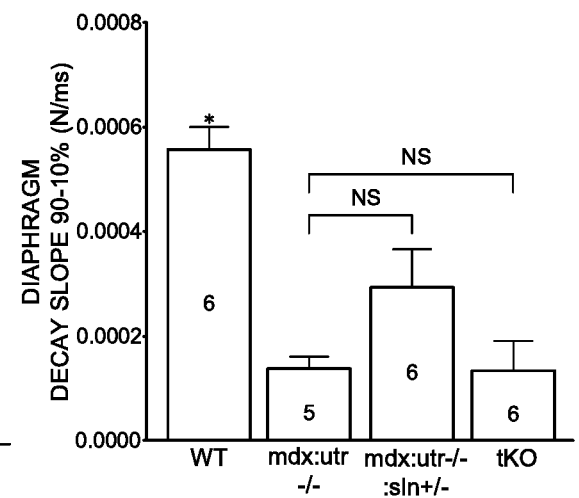

Next investigated was the effect of SLN ablation on muscle mechanics. The forelimb muscle grip strength was significantly increased in the mdx:utr−/−:sln+/− and tKO mice compared to that of mdx:utr−/− littermates (FIG. 7a). These studies were extended by measuring the isometric contractile properties of the dystrophic extensor digitorum longus (EDL; a less severely affected) and diaphragm (a more severely affected) muscles. The twitch-tension (FIG. 7b-7c), 10%-90% rising slope (rate of contraction) and 90%-10% decay slope (rate of relaxation) at 2 Hz (FIG. 8a-8b) and force-frequency curves (FIG. 7d) were significantly increased in the EDL muscle of mdx:utr−/−:sln+/− mice. These contractile parameters were also increased in the EDL of tKO mice but not at a statistically significant level. The half-maximal force stimulation frequency for EDL remained unaltered among the experimental groups [WT=27±3 (n=7), mdx:utr−/−=28±3 (n=5), mdx:utr−/−:sln+/−=26±2 (n=8) and tKO=28±1 (n=5) Hz; unpaired t-test with Welch's correction]. The effect of SLN ablation on diaphragm function in the mdx:utr−/− mice was less prominent. The twitch-tension at 2 Hz was significantly increased in the hemidiaphragm of mdx:utr−/−:sln+/− but not in the tKO mice (FIG. 7e-7f). The 10%-90% rising slope and 90%-10% decay slope obtained from the hemidiaphragm of mdx:utr−/−:sln+/− and tKO at 2 Hz showed a slightly increasing trend but were not significantly different from that of mdx:utr−/− controls (FIG. 8c-8d). Similarly, the force-frequency curves for the hemidiaphragm from mdx:utr−/−:sln+/− was shifted upwards but to a smaller extent in the tKO mice (FIG. 7g). The half-maximal force stimulation frequency for hemidiaphragm remained unaltered among all four mice groups [WT=11±0.3 (n=6), mdx:utr−/−=13±0.8 (n=5), mdx:utr−/−:sln+/−=12±0.5(n=6) and tKO=14±1.2 (n=6) Hz; unpaired t-test with Welch's correction]. These functional data corroborated the differences and structural improvements seen in the diaphragm of mdx:utr−/−:sln+/− and tKO mice (FIG. 5b). These findings suggest that reduction in SLN expression is sufficient to improve the functional properties of dystrophic skeletal muscles.

Figure 9A:
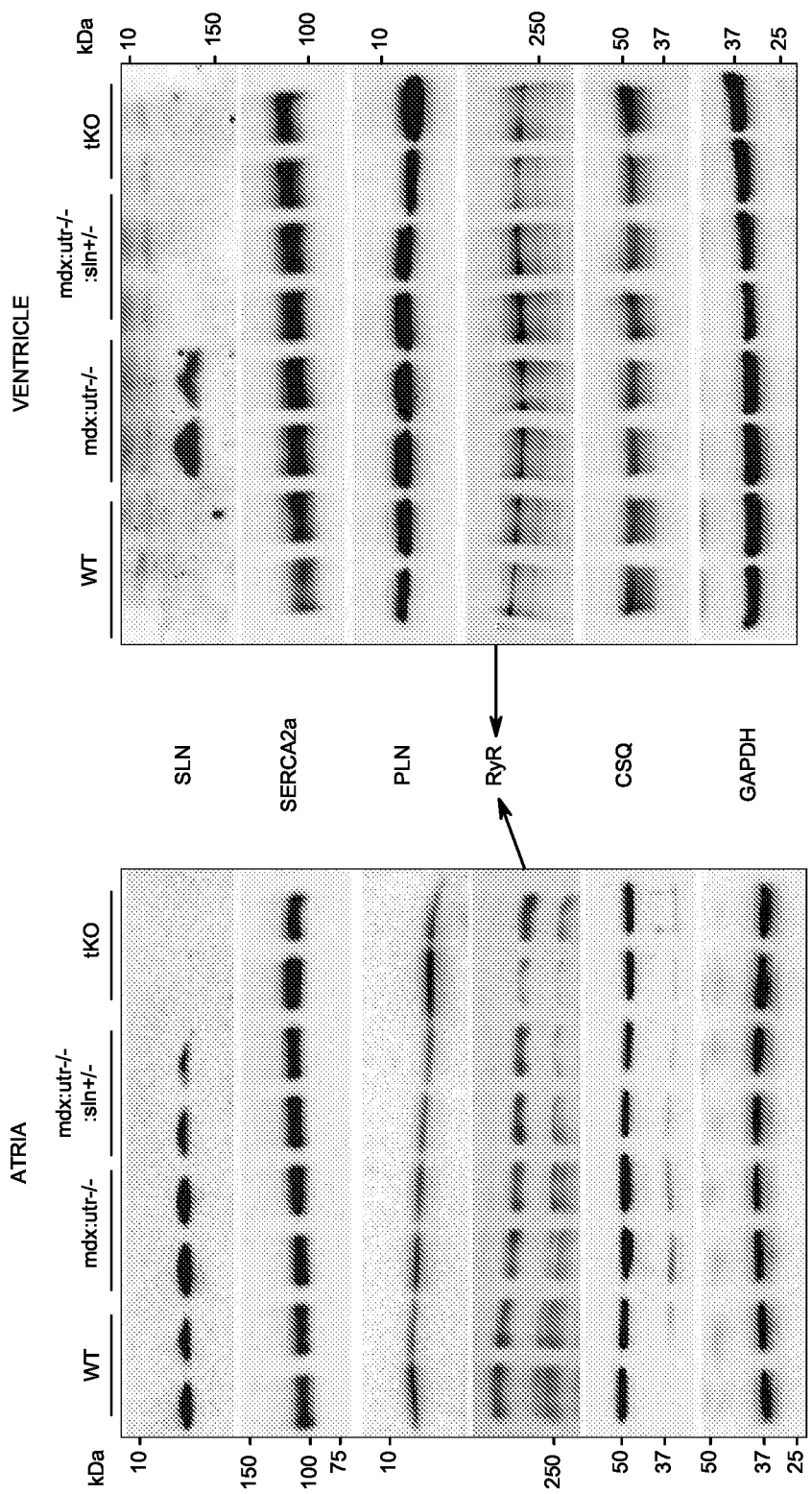
FIG. 9 shows that reducing SLN expression improves cardiac function in DMD. 9(a): Representative western blots (uncropped) showing SERCA2a, SLN, PLN, CSQ and RyR protein levels in atria and in the ventricles of WT, mdx: utr−/−, mdx:utr−/−:sln+/− and tKO mice. 9(b): Representative M-mode echocardiography images of left ventricles in 3-4 month old WT, mdx:utr−/−, mdx:utr−/−:sln+/− and tKO mice at baseline.
Figure 9B:
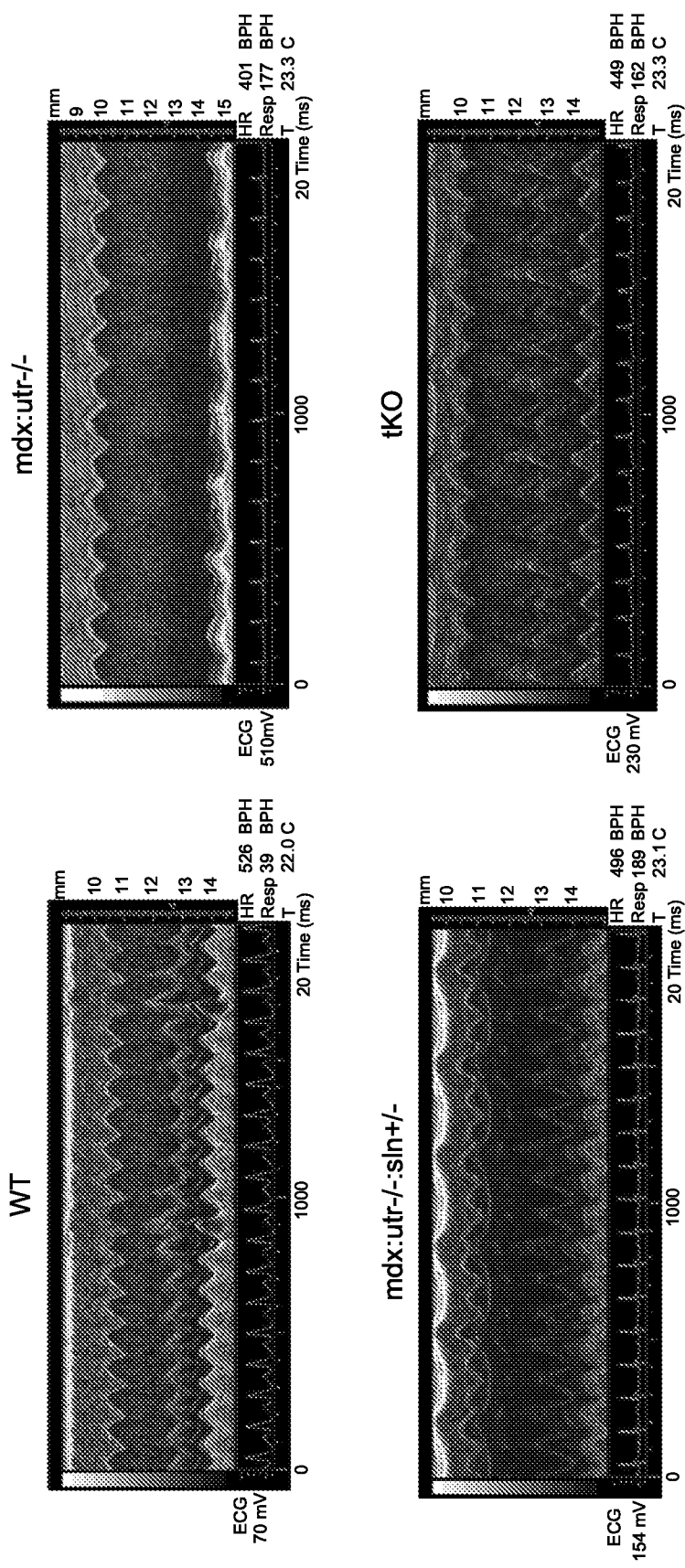
Figure 10A:
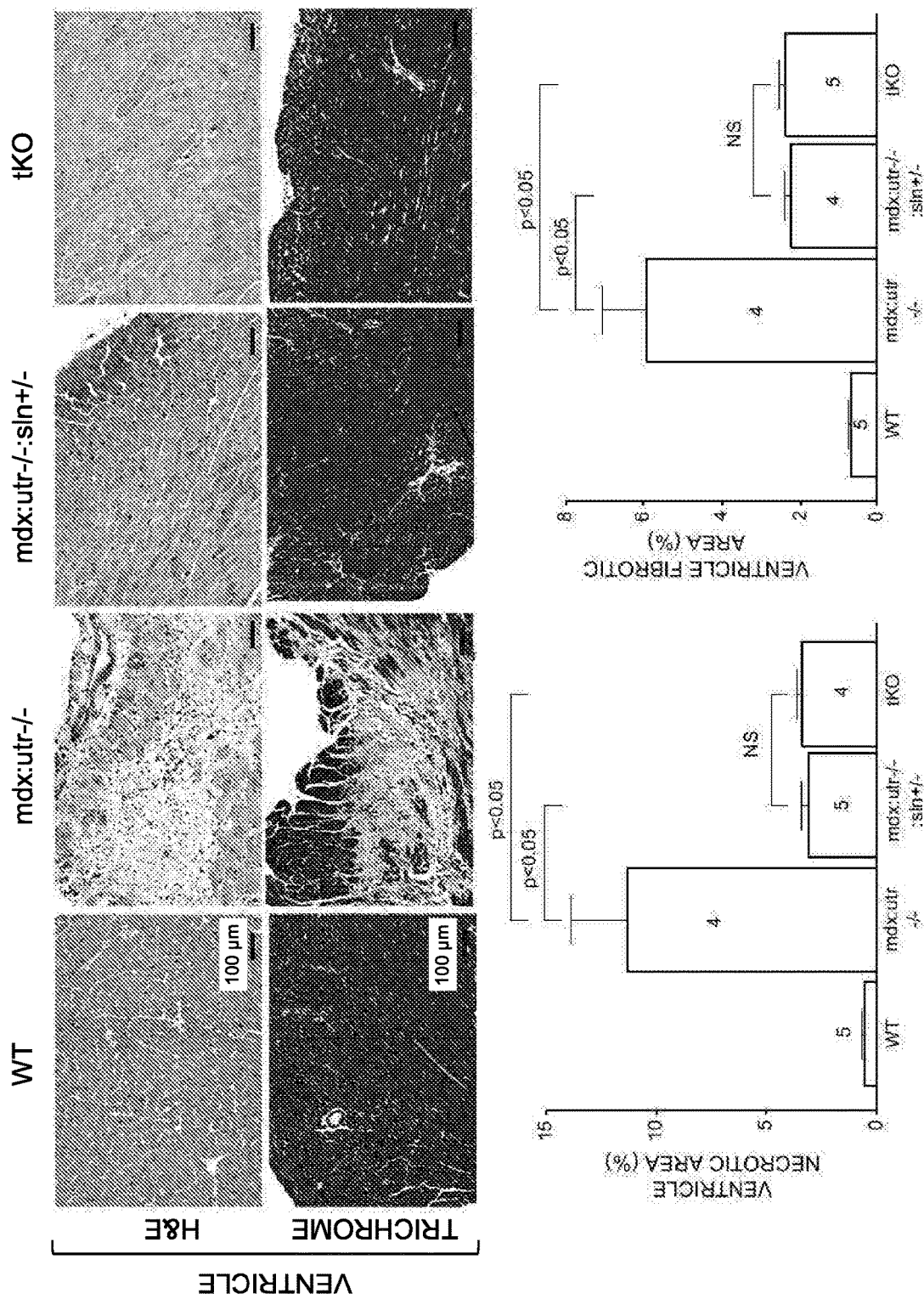
FIG. 10 shows that ablation of SLN expression prevents cardiomyopathy in mdx:utr−/− mice. All cardiac studies are performed in 3-4 month old mice. 10(a): Representative H&E and Masson's trichrome stained ventricular tissue sections. Original magnification is 10×. Scale bar, 100 μm. Bar graph indicate that reduction or ablation of SLN significantly reduced fibrosis and necrosis in the mdx:utr−/− hearts. The n number for each group and the p values (t-test with Welch's correction) are shown within the graph. Data are presented as mean±SEM. 10(b), 10(c): Echocardiographic measurements demonstrate that the left ventricular (LV) ejection fraction (EF) and fractional shortening (FS) are restored to normal values in the mdx:utr−/−:sln+/− and tKO mice. **$p<0.0001$ vs. other groups; n=6 per group. Data are presented as mean±SEM (t-test with Welch's correction).
Figure 10B:
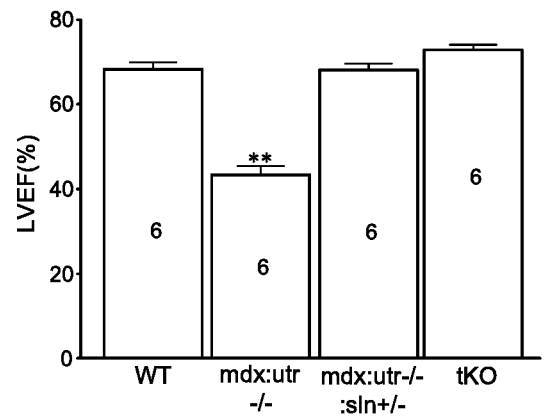
Figure 10C:
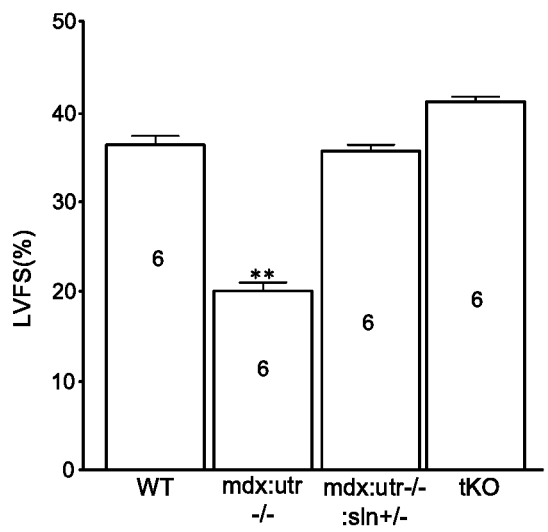

Ablation of SLN ameliorates dystrophic cardiomyopathy. Next it was determined whether SLN ablation ameliorates cardiac pathology in the mdx:utr−/− mice. Western blot analysis (FIG. 9a) and quantitation showed that loss of one SLN allele was sufficient to reduce SLN protein expression in atria (mdx:utr−/−=1.7±0.2 vs mdx:utr−/−:sln+/−=0.9±0.1 fold; n=4; p<0.05, t-test with Welch's correction) and in the ventricles of mdx:utr−/− mice near to WT levels. SLN ablation had no effect on the expression levels of SERCA2a, PLN, ryanodine receptor (RyR), and CSQ (FIG. 9a). H&E and trichrome staining and quantitation showed that mononuclear infiltration and fibrosis were significantly reduced in the mdx:utr−/−:sln+/− and tKO ventricles compared to that of mdx:utr−/− controls (FIG. 10a). Cardiac function evaluated by echocardiography (FIG. 9b) showed a marked improvement in left ventricular (LV) function as evident from the increased LV ejection fraction (EF; FIG. 10b) and fractional shortening (FS; FIG. 10c) in the mdx:utr−/−:sln+/− and tKO mice. There was an increase in interventricular septal end systole (IVSs) and posterior wall thickness along with significant reduction in LV internal diameter end diastole (LVIDd) in the mdx:utr−/−:sln+/− and tKO mice (Table 1). This finding suggested that hearts from these mice undergo specific concentric remodeling that contributes to the improved cardiac function. These findings indicate that normalizing SLN level is sufficient to preserve cardiac function and mitigate dystrophic cardiomyopathy in mice. These studies also suggest that $1 \times 10^{11}$ vg is sufficient to normalize SLN expression in mdx mice without any toxicity.

TABLE 1

Baseline echocardiographic data of 3-4 month old mice

| | WT | mdx:utr−/− | mdx:utr−/:sln+/− | mdx:utr−/−:sln−/− |
|---|---|---|---|---|
| IVSd, mm | 0.74 ± 0.05 | 0.83 ± 0.07 | 0.96 ± 0.05$ | 0.85 ± 0.07 |
| IVSs, mm | 1.28 ± 0.06 | 0.99 ± 0.05* | 1.39 ± 0.09 | 1.345 ± 0.08 |
| LVIDd, mm | 4.2 ± 0.13 | 3.5 ± 0.24$ | 3.34 ± 0.13$ | 3.25 ± 0.06$ |
| LVIDs, mm | 2.68 ± 0.07 | 2.81 ± 0.20 | 2.215 ± 0.10++ | 1.91 ± 0.03++ |
| LVPWd, mm | 0.63 ± 0.05 | 0.76 ± 0.07 | 0.78 ± 0.03 | 0.83 ± 0.09 |
| LVPWs, mm | 1.13 ± 0.03 | 0.83 ± 0.06* | 1.07 ± 0.05 | 1.21 ± 0.09 |

TABLE 1-continued

Baseline echocardiographic data of 3-4 month old mice

|        | WT       | mdx:utr−/− | mdx:utr−/−: sln+/− | mdx:utr−/−: sln−/− |
|--------|----------|------------|--------------------|--------------------|
| FS (%) | 36 ± 1.0 | 20 ± 0.8** | 36 ± 1.0           | 41 ± 0.4#          |
| EF (%) | 69 ± 1.5 | 44 ± 1.8** | 68 ± 0.6           | 73 ± 0.4#          |
| HR, bpm| 466 ± 16 | 498 ± 52   | 531 ± 47           | 529 ± 25           |

IVSd—interventricular septal end diastole, IVSs—interventricular septal end systole, LVIDd—left ventricular internal diameter end diastole, LVIDs—left ventricular internal diameter end systole, LVPWd—left ventricular posterior wall end diastole, LVPWs—left ventricular posterior wall end systole, FS—fractional shortening, EF—ejection fraction, HR—heart rate.
$^\$ p < 0.005$ vs. WT; $^*p < 0.05$ vs. other groups; $^{**}p < 0.0001$ vs. other groups; $^\#p < 0.05$ vs. WT & mdx:utr−/−:sln+/−; $^{++}p < 0.05$ vs WT & mdx:utr−/−; n = 6 per group.
Data are presented as mean ± SEM.

Figure 11A:
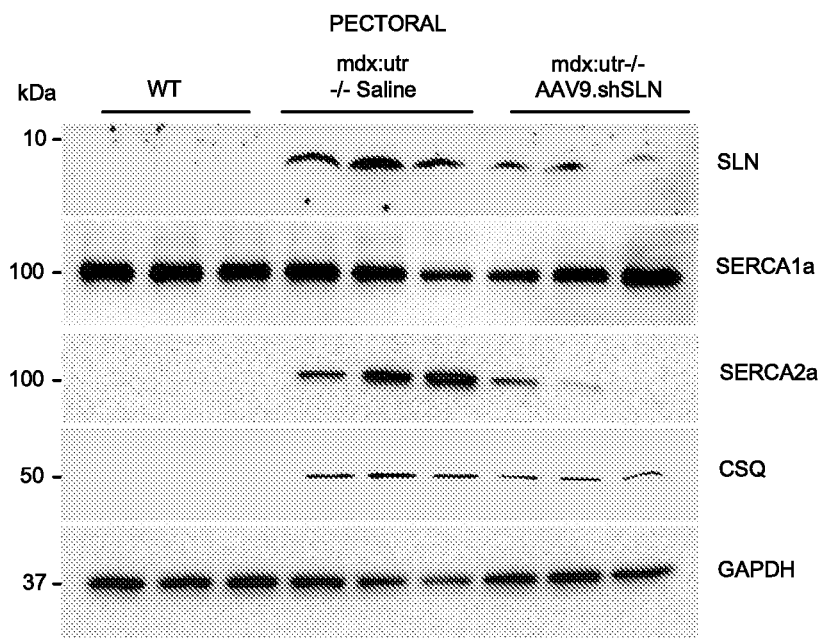
FIGS. 11(a); and 14(e)
Figure 11B:
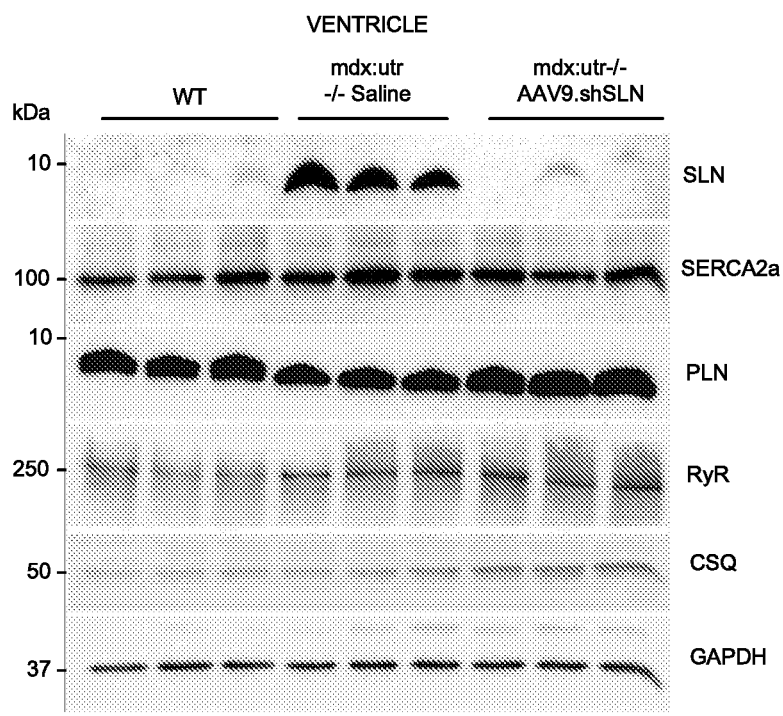
FIG. 11(b).

Postnatal AAV9 SLN shRNA gene therapy mitigates DMD. Findings from the above studies suggest that normalizing SLN expression is sufficient to mitigate the severe DMD phenotype including muscle pathophysiology, diaphragm function and cardiomyopathy. To translate these findings into a therapeutic strategy, SLN expression was knocked down postnatally in one-month old mdx:utr−/− mice via AAV9 mediated expression of SLN specific short-hairpin RNA (shSL/V). The AAV9.shSLN treatment for 12 weeks significantly reduced SLN expression in both skeletal muscle (0.22-fold vs saline treated controls; p<0.05) and LV (similar to WT) of mdx:utr−/− mice (FIG. 11a-11b and FIG. 12a-12b). In the mdx:utr−/− myocardium, AAV treatment had no effect on the protein expression of SERCA2a, PLN, CSQ and RyR (FIG. 11b). On the other hand, AAV treatment reduced SERCA2a (p<0.05) and CSQ (p<0.07) protein levels in the pectoral muscles of mdx:utr−/− mice (FIG. 11a and FIG. 12a). These data are consistent with the findings on the mdx:utr−/−:sln+/− mice (FIG. 4g) and suggest that postnatal reduction in SLN expression can also restore the SR function in the mdx:utr−/− mice.

Figure 11C:
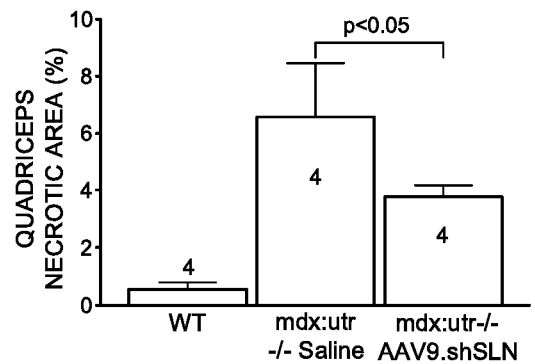
FIG. 11 shows that postnatal AAV9.shSLN treatment ameliorates DMD and associated cardiomyopathy in mdx: utr−/− mice. One-month old male and female mice were injected with AAV or saline and experiments were performed 12 weeks post-injection. 11(a), 11(b): Representative Western blots show that AAV9.shSLN treatment effectively reduces SLN expression in skeletal (pectoral muscle) and cardiac (ventricle) muscles. Uncropped scans of Western blots are shown in FIGS. 14(d) and 14(e). The AAV treatment reduced SERCA2a and CSQ levels in the pectoral muscles of mdx:utr−/− mice. 11(c), 11(d): Quantitation of areas with mononuclear infiltration in the H&E stained tissue sections show that cell necrosis is significantly reduced in both quadriceps and ventricles of AAV treated mdx:utr−/− mice compared to that of saline injected mdx: utr−/− controls. Data are presented as mean±SEM. The n number for each group and the p values (t-test with Welch's correction) are shown within the graph. 11(e): LV EF; 11(f): forelimb muscle strength; and 11(g), 11(h): the maximum twitch force generated by EDL and hemidiaphragm at 2 Hz are significantly improved in the AAV treated mice compared to that of saline injected mdx:utr−/− controls. **$p<0.0001$ vs. other groups. Data are presented as mean±SEM. The n number for each group and the p values (t-test with Welch's correction) are shown within the graph.
Figure 11D:
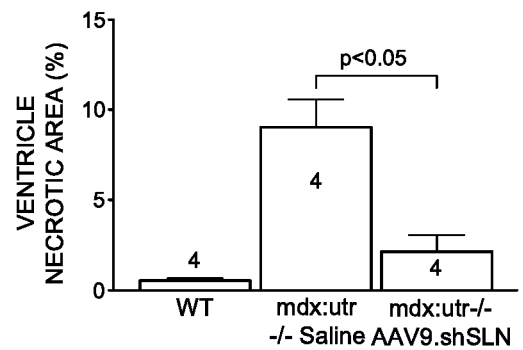
Figure 11E:
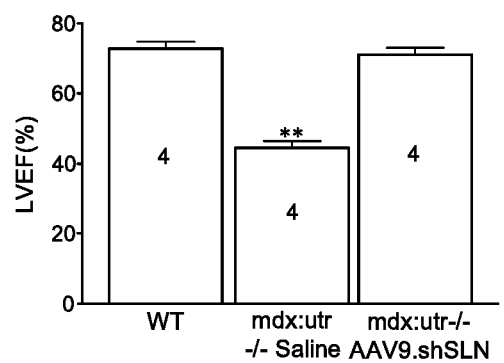
Figure 11F:
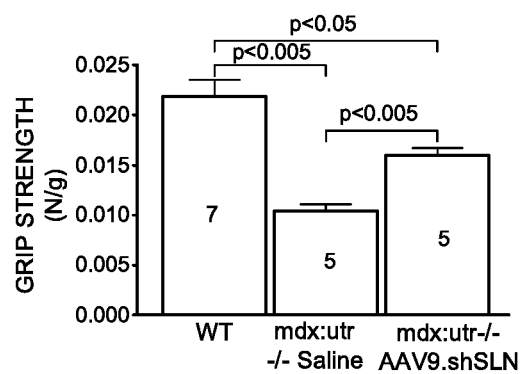
Figure 11G:
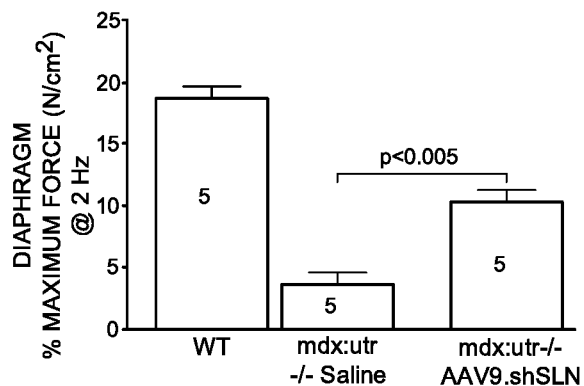
Figure 11H:
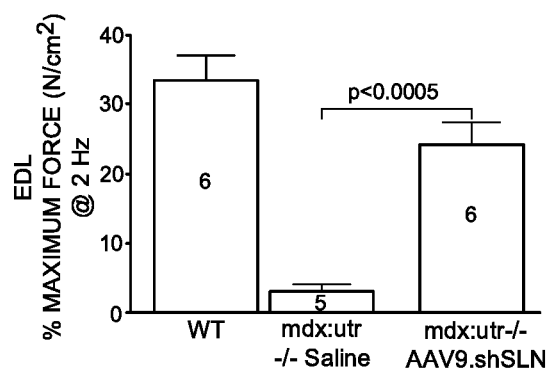
Figure 13A:
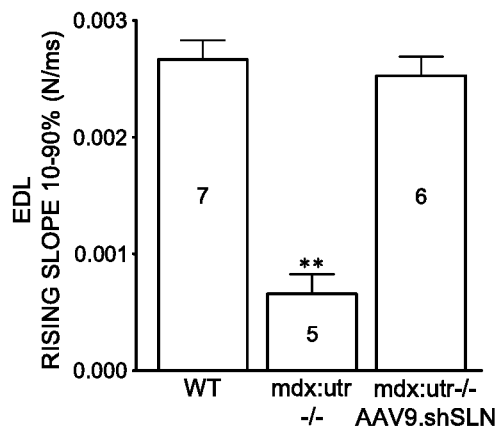
FIG. 13 shows AAV9.shSLN treatment improves muscle function in DMD mice. 13(a), 13(b): The EDL from AAV treated mice exhibits increased rate of contraction as represented by 10%-90% rising slope and the rate of relaxation as represented by 90%-10% decay slope at 2 Hz in comparison with that of mdx:utr−/− mice. 13(c), 13(d): These changes were less prominent in the diaphragm of AAV treated mdx:utr−/− mice. The n number for each group is shown within the bar. **significantly different from other groups ($p<0.005$, t-test with Welch's correction). 13(e), 13(f): Force-frequency relationship curve indicates that muscle force is significantly improved at all frequencies in both EDL and diaphragm of AAV treated mdx:utr−/− mice. Data are presented as mean±SEM.
Figure 13B:
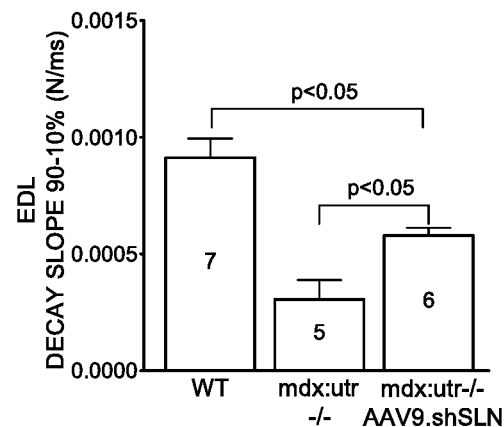
Figure 13C:
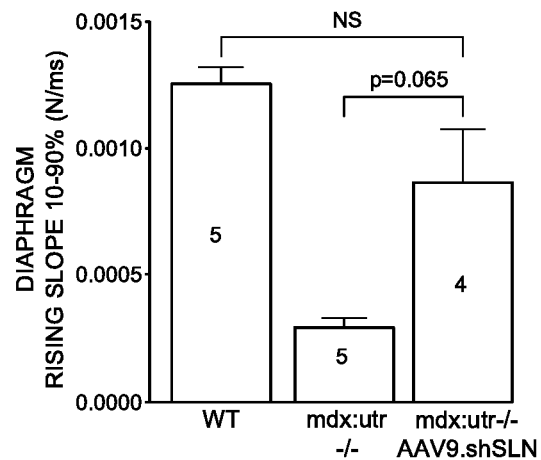
Figure 13D:
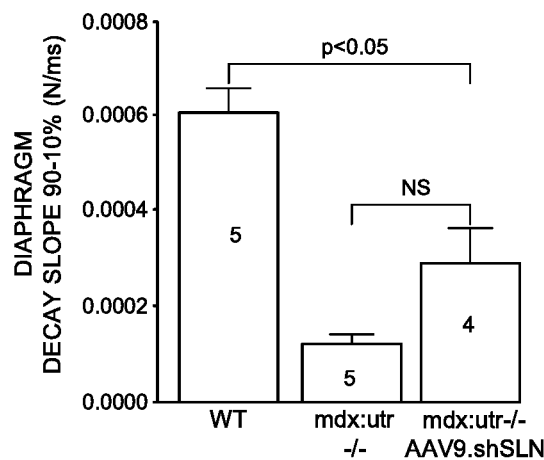
Figure 13E:
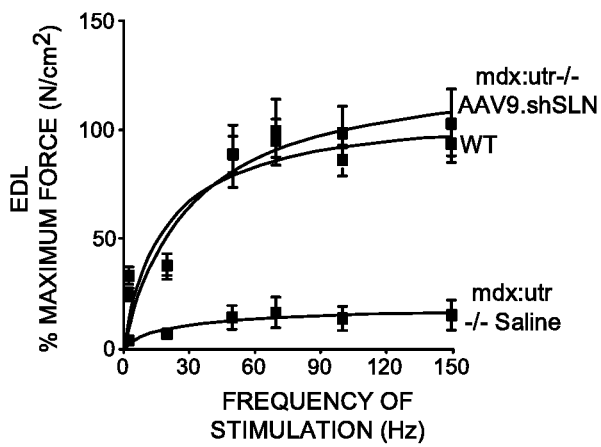
Figure 13F:
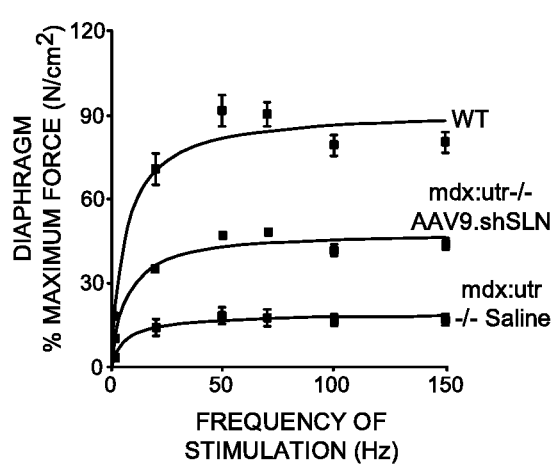

It was next determined whether AAV gene therapy mitigates cardiac and skeletal muscle pathophysiology in the mdx:utr−/− mice. The outcome of these studies mimics the data from the mdx:utr−/−:sln+/− mice. H&E staining (FIG. 12c) and quantitation showed that the invasion of mononuclear cells and cell necrosis were significantly reduced both in the skeletal muscle (FIG. 11c) and in the ventricles (FIG. 11d) of AAV treated mdx:utr−/− mice. AAV treatment also improved the LV systolic function and cardiac remodeling (FIG. 11e and Table 2) in mdx:utr−/− mice. Forelimb muscle strength was significantly improved in AAV treated mdx:utr−/− mice (FIG. 11f). Furthermore, the twitch-tension (FIG. 11g-11h), measured as 10%-90% rising slope and 90%-10% decay slope at 2 Hz and force-frequency relationships, (FIG. 13a-13f) were significantly increased in both EDL and hemidiaphragm of AAV treated groups indicating improved muscle mechanics. Together these findings suggest that AAV mediated postnatal reduction in SLN expression is sufficient to mitigate the severe muscular dystrophy and associated cardiomyopathy in mdx:utr−/− mice. It was shown that either reduction or total loss of SLN equally improved the LV function and reduced the myocardial fibrosis and necrosis in mdx:utr−/− mice.

TABLE 2

Baseline echocardiographic data of AAV treated mdx:utr−/− mice

|          | WT          | mdx:utr−/− Saline | mdx:utr−/− AAV9.shSLN |
|----------|-------------|-------------------|------------------------|
| IVSd, mm | 0.90 ± 0.04 | 0.95 ± 0.14       | 0.78 ± 0.08            |
| IVSs, mm | 1.31 ± 0.04 | 0.98 ± 0.08*      | 1.3 ± 0.08             |
| LVIDd, mm| 4.06 ± 0.11 | 3.1 ± 0.24$       | 3.12 ± 0.1$            |
| LVIDs, mm| 2.58 ± 0.07 | 2.43 ± 0.20       | 1.89 ± 0.09#           |
| LVPWd, mm| 0.77 ± 0.08 | 0.72 ± 0.06       | 0.9 ± 0.09             |
| LVPWs, mm| 1.12 ± 0.06 | 0.89 ± 0.05*      | 1.02 ± 0.09            |
| FS(%)    | 37 ± 0.6    | 22 ± 1.0**        | 40 ± 1.4               |
| EF(%)    | 73 ± 2.3    | 44 ± 1.8**        | 71 ± 1.8               |
| HR, bpm  | 449 ± 27    | 585 ± 7$          | 559 ± 58               |

IVSd—interventricular septal end diastole, IVSs—interventricular septal end systole, LVIDd—left ventricular internal diameter end diastole, LVIDs—left ventricular internal diameter end systole, LVPWd—left ventricular posterior wall end diastole, LVPWs—left ventricular posterior wall end systole, FS—fractional shortening, EF—ejection fraction, HR—heart rate.
$^\$ p < 0.05$ vs. WT; $^*p < 0.05$ vs. other groups; $^{**}p < 0.005$ vs. other groups; $^\#p < 0.06$ vs. other groups.
n = 4 per group.
Data are presented as mean ± SEM.

In summary, these findings suggest that reduction in SLN expression is sufficient to improve the SERCA function in dystrophic muscles. Systemic injection of AAV9.shSLN reduced SLN expression in both heart and skeletal muscles. Furthermore, reduction in SLN protein expression ameliorated the severe muscular dystrophy phenotype, and extended the lifespan of mdx:utr−/− mice. These findings also suggest that reduction in SLN expression can improve the muscle regeneration process and prevent fiber-type transition in dystrophic muscles.

Methods

Animal studies: All experimental procedures involving mice in this study were approved by the Institutional Animal Care and Use Committee (IACUC) of New Jersey Medical School, Rutgers, Newark, N.J. The tissue samples from normal and DMD dogs were from studies approved by the IACUC of University of Missouri, Columbia, Mo.

Mice: 3-4 months old male and female mice in C57BL/6 background were used for all the experiments described in this study. The mdx:utr−/−:sln+/− and tKO (mdx:utr−/−: sln−/−) mice were generated by crossing the mdx:utr+/− mice to sln−/− mice. These mice were crossed for five generations to obtain the mdx:utr+/−:sln+/− mice in isogenic background. The male and female mdx:utr+/−:sln+/− mice were then crossed to generate the mdx:utr−/−, mdx:utr−/−: sln+/− and tKO mice. Mice were kept under a 12-hour light/dark cycle with a temperature of 22-24° C. and 60-70% of humidity and fed ad libitum with normal chow diet. The genotypes of the mice were identified by PCR analysis using previously published sequences. Animal numbers were pre-determined based on pilot studies and sample sizes were similar to generally employed in the field. No samples, mice or data points were excluded from the data analysis. Animals were not randomized except for the genotypes. For echocardiography and muscle force measurements, investigators were blinded for the genotypes. The tissues used for various biochemical, histopathological and functional analyses are shown below.

| Name of the assay      | Tissues used                                              |
|------------------------|-----------------------------------------------------------|
| Western blot analysis  | Atria, ventricles, diaphragm, quadriceps and pectoral muscle |

| Name of the assay | Tissues used |
|---|---|
| Histopathology | Quadriceps, diaphragm and ventricles |
| Immunostaining | Pectoral muscle |
| Calpain assay | Pectoral muscle |
| Muscle physiology | EDL and diaphragm |

Experimental dogs: All dog-related experiments were approved by the IACUC of the University of Missouri and were performed in accordance with NIH guidelines. All the experimental dogs were on a mixed genetic background consisting of golden retriever, labrador retriever, Corgi and beagle and generated in house at the University of Missouri by artificial insemination. Affected dogs carry various mutations in the dystrophin gene that abort dystrophin expression. The genotype was determined by polymerase chain reaction according to published protocols. The diagnosis was confirmed by the significantly elevated serum creatine kinase level in affected dogs. All experimental dogs were housed in a specific-pathogen free animal care facility and kept under a 12-hour light/12-hour dark cycle. Affected dogs were housed in a raised platform kennel while normal dogs were housed in regular floor kennel. Depending on the age and size, two or more dogs are housed together to promote socialization. Normal dogs were fed dry Purina Lab Diet 5006 while affected dogs were fed wet Purina Proplan Puppy food. Dogs were given ad libitum access to clean drinking water. Toys were allowed in the kennel with dogs for enrichment. Dogs were monitored daily by the caregiver for overall health condition and activity. A full physical examination was performed by the veterinarian from the Office of Animal Research at the University of Missouri for any unusual changes (such as behavior, activity, food and water consumption, and clinical symptoms). Both male and female dogs were used for this study. The non-DMD controls were in the age range of 1.73 to 31 month old and the DMD dogs were in the age range of 6.8 to 11.9 month old. Experimental subjects were euthanized at the end of the study according to the 2013 AVMA Guidelines for the Euthanasia of Animals. Freshly dissected ECU muscle was snap frozen in liquid nitrogen in blocks of ~0.5 to 1 cm$^3$. Frozen muscle tissues were kept in an −80° C. freezer until use.

Human Samples: Two non-DMD and two DMD male human ventricular samples obtained from the University of Maryland Brain and Tissue Bank, a member of the NIH NeuroBioBank network, were used for this study. All samples were dissected post-mortem. DMD1 cause of death was attributable to cardiac failure at age 15; while DMD2 cause of death was attributed to pulmonary thromboembolism at age 17. The research use of these samples was approved by the Institutional Review Board (IRB) at Rutgers New Jersey Medical School.

The research use of the human quadriceps tissues was approved by the IRB at the Ohio State University/Nationwide Children's Hospital and performed in accordance with relevant guidelines and regulations. The two non-DMD human quadriceps were from a 4-year-old and 6-year-old normal child. The two DMD quadriceps were from 11 and 15-year-old DMD patients. Informed consent was obtained from all subjects from whom tissues were analyzed.

AAV9.shSLN generation and delivery into mdx:utr−/− mice: The shSLN sequence (ACTTCACAGTTGTCCT-CATCACTCGAGTGATGAGGACAACTGTGAAG) (SEQ ID NO: 2) was first cloned into plasmid pds-shPLB using HindIII and BamHI sites to replace the shPLB sequence. The entire 975 bp AAV cassette (ITR-U6-promoter-shSLN-bgHpA-ITR) and also some plasmid backbone regions flanking the ITRs were digested out with BspHI and inserted into pFastBacDual at the NcoI site. The resulting plasmid "pFB-ITR-sh-SLN" was used to create a recombinant Baculovirus "Bac-ITR-sh-SLN" using the Bac-to-Bac System (Invitrogen). The AAV9.shSLN was produced in Sf9 insect cells as previously described (Urabe et al., Hum. Gene Ther. 13, 1935-1943 (2002)). Briefly, Sf9 insect cell lines were infected with Bac-ITR-sh-SLN, BacRep and BacCap9 viruses. After 3 days post-infection, cells were harvested and the AAV was purified by iodixanol gradient ultracentrifugation and dialyzed into Lactated Ringer's. The viral titers were determined by qPCR using primers binding the bGH region (forward: 5'TGCCTTCCTTGACCCT (SEQ ID NO: 3); reverse: 5' CCTTGCTGTCCTGCCC (SEQ ID NO: 4)) and dilutions of the AAV2 Reference Standard Material (ATCC) to generate a standard curve.

For AAV9.shSLN injection studies, one-month old male and female mdx:utr−/− mice were used. Mice were divided into two groups: the AAV-treated group and the saline treated group. 6 mice were used per group. The AAV9.shSLN vector ($1 \times 10^{11}$ genome) was delivered to the mice via a single bolus tail vein injection. The mice were sacrificed 16 weeks of age after measuring the forelimb strength and cardiac function by M-mode echocardiography and the tissues were used for functional and biochemical studies.

Isometric force measurements: Isometric force in isolated muscle tissues was determined as previously described. Briefly, hemidiaphragm and EDL were harvested immediately following euthanasia and kept in cold oxygenated Ringer's solution (in mmole/liter, 135 NaCl, 5 KCl, 1 $MgCl_2$, 2 $CaCl_2$, 1 $Na_2HPO_4$, 15 $NaHCO_3$, and 5.5 glucose). Hemidiaphragm and EDL preparations were mounted in a Rodnoti chamber (Rodnoti Glass Technology, Inc., Calif., USA) containing oxygenated (95% $O_2$-5% $CO_2$) Ringer's solution at room temperature (~22° C.). One tendon was attached to the bottom of the Rodnoti chamber while the other tendon was attached to a Grass force transducer. For direct stimulation of muscles, two parallel plate ($1 \times 1$ cm$^2$) silver electrodes that were attached to the inner wall of Rodnoti chamber to deliver 1 millisecond long square electric pulses produced by a Grass stimulator. Muscles were adjusted to the optimal length (Lo) for force generation. At the end of the protocol, muscle length and weight were measured using a Vernier caliper and weighing scale respectively. To detect the threshold stimulation, the stimulation voltage was increased till maximal force of contraction was achieved. Trains of 40 suprathreshold (120% of threshold) stimuli ranging from 2-150 Hz were applied to study the muscle force generation. The response signals were digitized (Digidata 1440A Axon Instruments), acquired, and analyzed using PCLAMP software (version 10.1, Axon Instruments). Muscle cross sectional area (CSA) for force normalization was calculated using the following formula as previously described. CSA=m/(Lo×L/Lo×1.06 mg/mm$^3$), where "m" is muscle mass (in mg), Lo is optimal muscle length, L/Lo is ratio of fiber length to muscle length (0.45 for EDL and 1 for diaphragm) and 1.06 mg/mm$^3$ is muscle density.

Histological analysis: Five micron paraffin sections of various skeletal and cardiac tissues from WT, mdx:utr−/−, mdx:utr−/−:sln+/− and tKO mice were stained with Hematoxylin and Eosin (H&E) and Masson's trichrome following standard procedures. The red stained collagen areas by trichrome staining indicating fibrosis and necrotic areas containing mononuclear cells stained by H&E were calculated using NIH ImageJ 1.43u program.

Immunofluorescence: The mouse monoclonal antibodies specific for eMyHC (BF45) and type 1 MyHC (BAF8) were purchased from Developmental Studies Hybridoma Bank. Tissues were cryo-sectioned at 10 microns and immunostained using antibodies specific for eMyHC (1:10) or type 1 MyHC (1:5) overnight at 4° C. and processed as previously described. For fiber size measurements, the tissue sections were stained with WGA, (fluorophore conjugated, 1:100, Cat. #W11262, Life Technologies). Images were obtained using a Zeiss LSM 510 on Zeiss Axiovert 100M Base and processed using NIS Elements. The minimal "Feret's" diameter variance coefficients of the muscle fiber size was calculated on the WGA stained sections using the ImageJ 1.43u program.

Figures 14A, 14B, 14C:
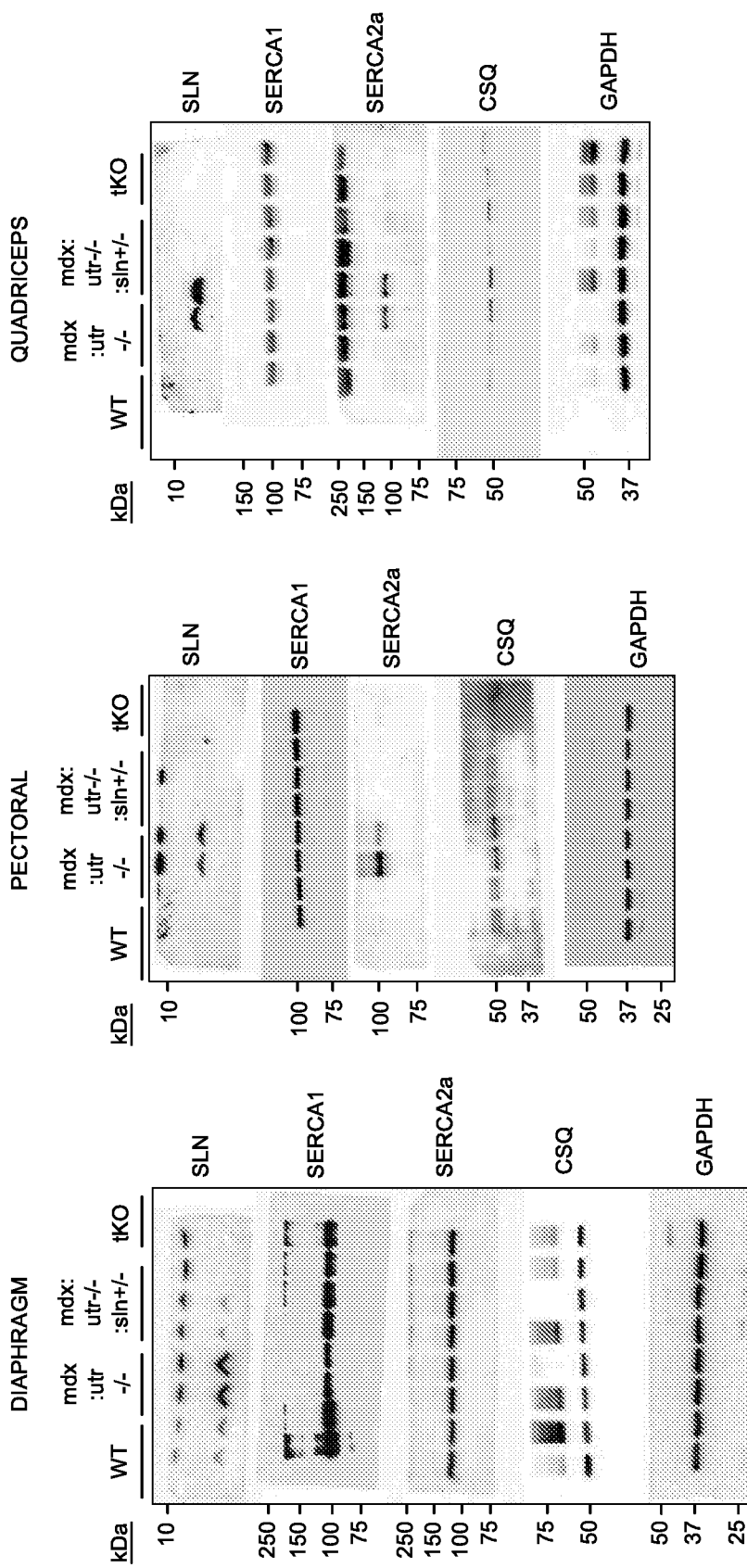
FIG. 14 shows uncropped Western images. Western images are corresponding to the images shown in 14(a)
Figures 14D, 14E:
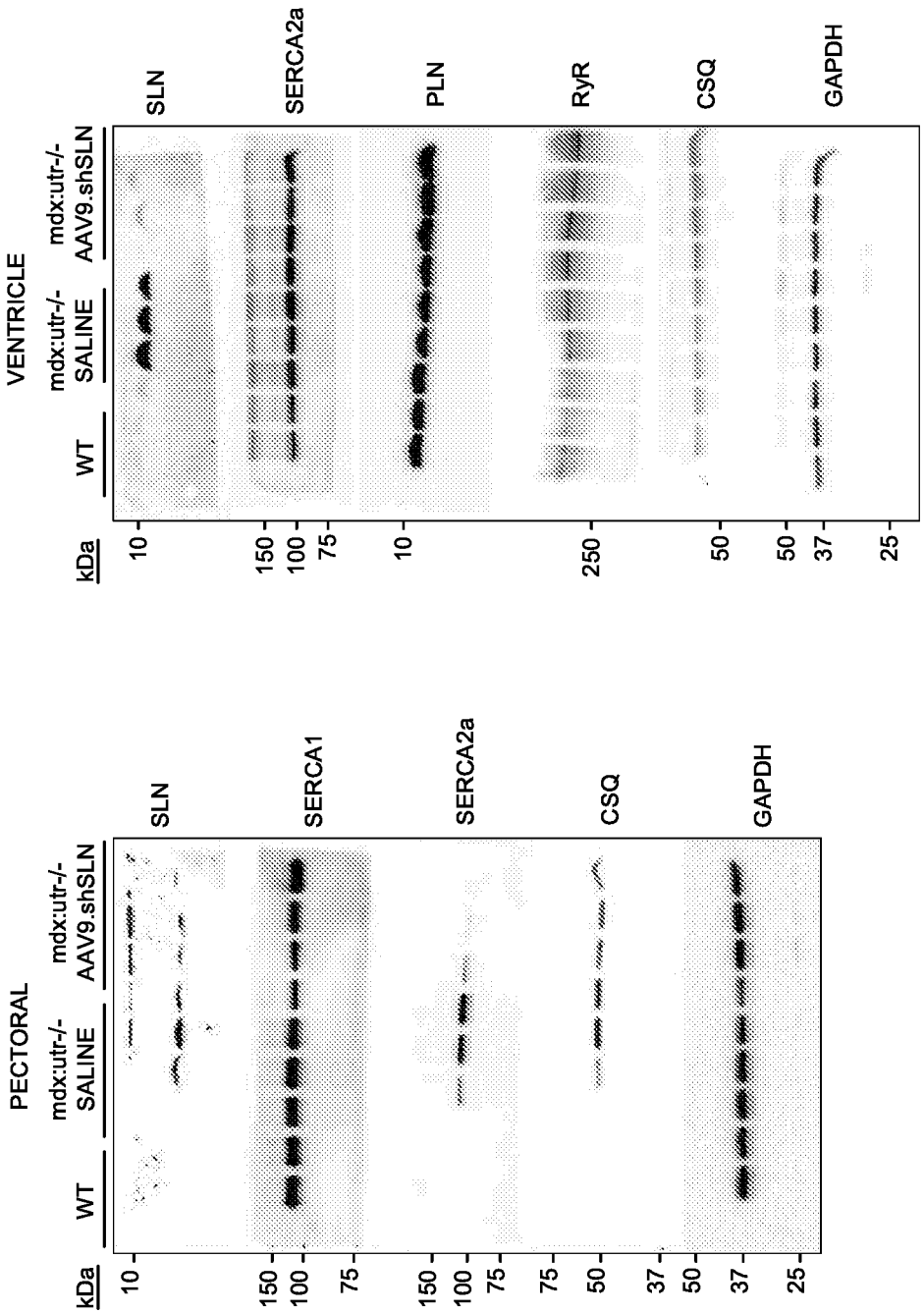
Figure 15A:
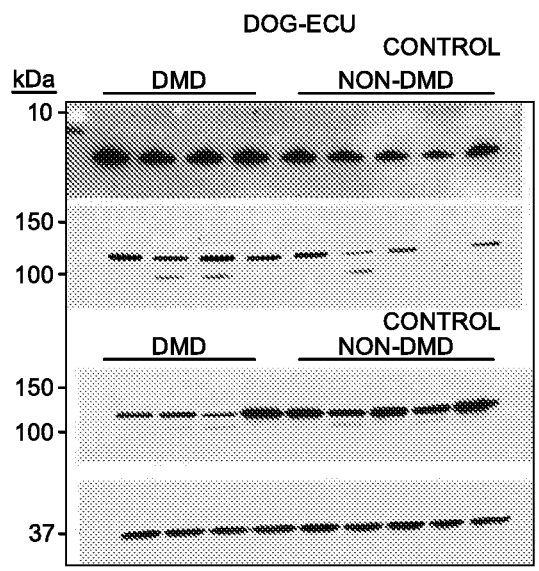
FIG. 15 shows uncropped Western images. Western images are corresponding to the images shown in 15(a)
Figure 15B:
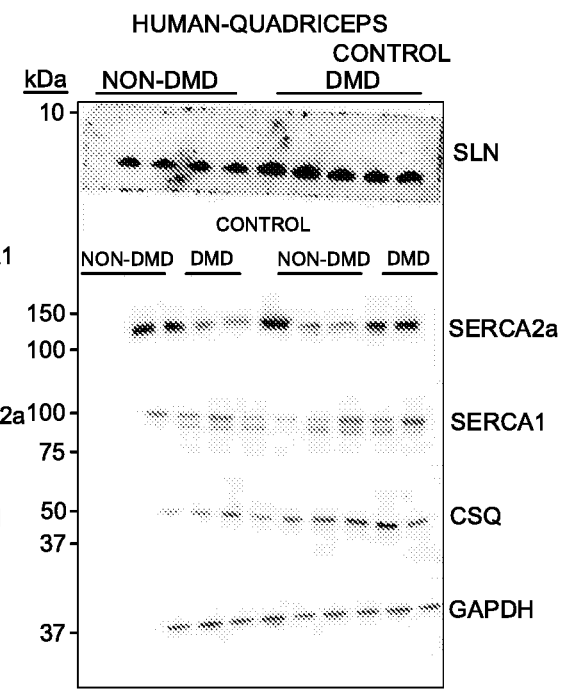
Figure 15C:
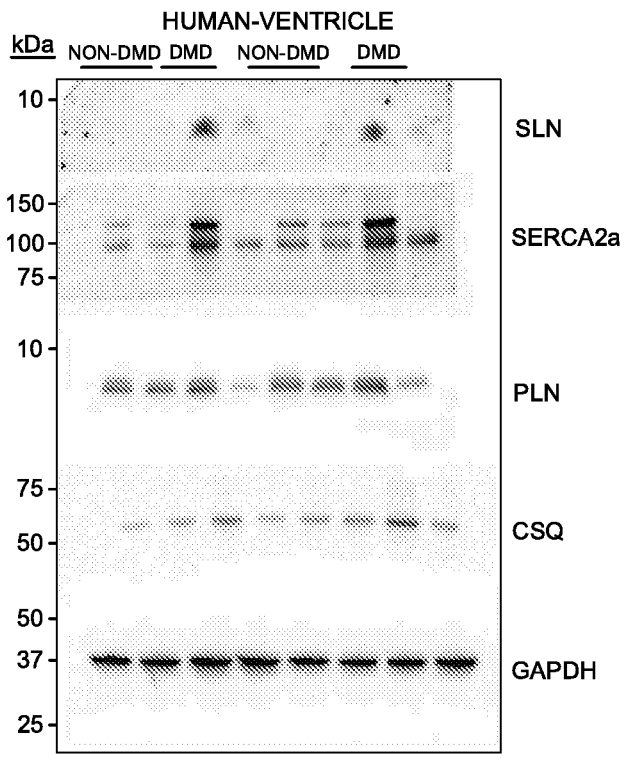

Western blot analysis: Mouse tissues were dissected out, rinsed in sterile PBS, and flash frozen in liquid nitrogen. Mouse, dog or human tissue homogenization was performed in lysis buffer (in mmole/liter, 50 Tris, pH 7.4, 150 NaCl, 1 EDTA and 0.5% NP-40) supplemented with PMSF (1 mmole), $NaVO_3$ (5 mmole), Okadaic Acid (10 nmole), NaF (1 mmole), and benzamidine (1 mmole). Equal amounts of total protein extracts were separated on the sodium dodecyl sulfate-polyacrylamide gels (SDS-PAGE) along with pre-stained molecular weight markers and transferred to nitrocellulose membranes for 1 hour at room temperature. After transfer, the membranes were stained with Ponceau S and cut into small stripes based on the molecular weight of each protein studied. The membrane strips were then blocked with 3% milk in phosphate-buffered saline, and probed overnight at 4° C. using antibodies specific for SLN (anti-rabbit, 1:3000), SERCA1 (anti-rabbit, 1:2000, custom made), SERCA2a (anti-rabbit, 1:5000, custom made), PLN (anti-rabbit, 1:3000, custom made), CSQ (anti-rabbit, 1:5000, Affinity Bio Reagents) which recognizes both cardiac and skeletal isoforms, RyR (anti-mouse, 1:1000, Affinity BioReagents) or GAPDH (anti-mouse, 1:10,000, Sigma). Membranes were incubated with appropriate secondary antibodies for 45 minutes at room temperature and visualized with SuperSignal West Dura Substrate kit (ThermoFisher Scientific) using Bio-Rad ChemiDoc MP Imaging system. Quantitation of signals were performed using Image Lab version 5.1 software and then normalized to GAPDH levels. Western blots were repeated at least three times. Uncropped scans of the Western images are shown in FIGS. 14 and 15.

Grip-strength measurements: An assessment of muscle function was recorded using grip strength meter (Columbus Instruments). The grip strength meter was positioned horizontally and the mouse was held by its tail and allowed to securely grip the triangular pull bar. After the mouse obtained a solid grasp of the triangular pull bar, the mouse was pulled backward parallel to the device. The force that was applied to the bar at the time of release was recorded as the peak grip strength (Newton). This was repeated three times and an average force was determined for each mouse. Grip strength values were normalized by the weight (g) of each animal to get the grip strength (N/g) ratio.

SR $Ca^{2+}$ uptake: SR $Ca^{2+}$ uptake was measured following the Millipore filtration technique as previously described. Briefly, about 150 µg of the total protein extract was incubated at 37° C. in 1.5 ml of $Ca^{2+}$ uptake medium (in mmol/liter, 40 imidazole, pH 7.0, 100 KCl, 5 $MgCl_2$, 5$NaN_3$, 5 potassium oxalate, and 0.5 EGTA) and various concentrations of $CaCl_2$ to yield 0.03-3 µmol/liter free $Ca^{2+}$ (containing 1 µCi/µmol $^{45}Ca^{2+}$). To obtain the maximal stimulation of SR $Ca^{2+}$ uptake, ruthenium red was added to a final concentration of 1 µmole immediately prior to the addition of the substrates to begin the $Ca^{2+}$ uptake. The reaction was initiated by the addition of ATP to a final concentration of 5 mmole and terminated at 1 min by filtration. Each assay was performed in duplicate. The rate of SR $Ca^{2+}$ uptake and the $Ca^{2+}$ concentration required for $EC_{50}$ were determined by non-linear curve fitting analysis using GraphPad Prism v6.01 software.

Calpain assay: Activated calpain in the protein extract was measured using a calpain activity assay kit (Abcam, Cat. #ab65308). Briefly, cytosolic protein extracts of pectoral muscle were prepared with the extraction buffer which prevents the auto-activation of calpain during the extraction procedure. The calpain activity was measured using fluorometric assay using calpain substrate Ac-LLY-AFC. The activity was represented as relative fluorescence units (RFU)/mg protein.

Echocardiography: Mice were anesthetized with 2.5% tribromoethanol and echocardiography was performed using the high resolution ultrasound machine VisualSonic/Vevo 770 system with a high frequency transducer (30 MHz) as previously described. Left ventricular (LV) dimensions, wall thicknesses, LV fractional shortening (FS), and LV ejection fraction (EF) were measured from the LV M-Mode images.

Statistical analysis: The established DMD-standard operating procedures were followed for outcome measurements for fiber-size, quantitation of fibrosis and necrosis and muscle mechanics. All statistical analyses were performed using GraphPad Prism v6.01 software. Results are presented as the mean±SEM. Differences were determined using a two-tailed, unpaired Student's "t" test with Welch's correction. Two-way analysis of variance (ANOVA) with post-hoc Bonferroni correction were used for multi-group comparison when necessary. A value of $p<0.05$ was considered as significant. The survival curve was generated using Kaplan-Meier survival analysis and data was analyzed using log-rank (Mantel-Cox) test.

Example 2

Increasing SLN Protein Levels in Canine Dystrophic Myoblasts

Figure 16:
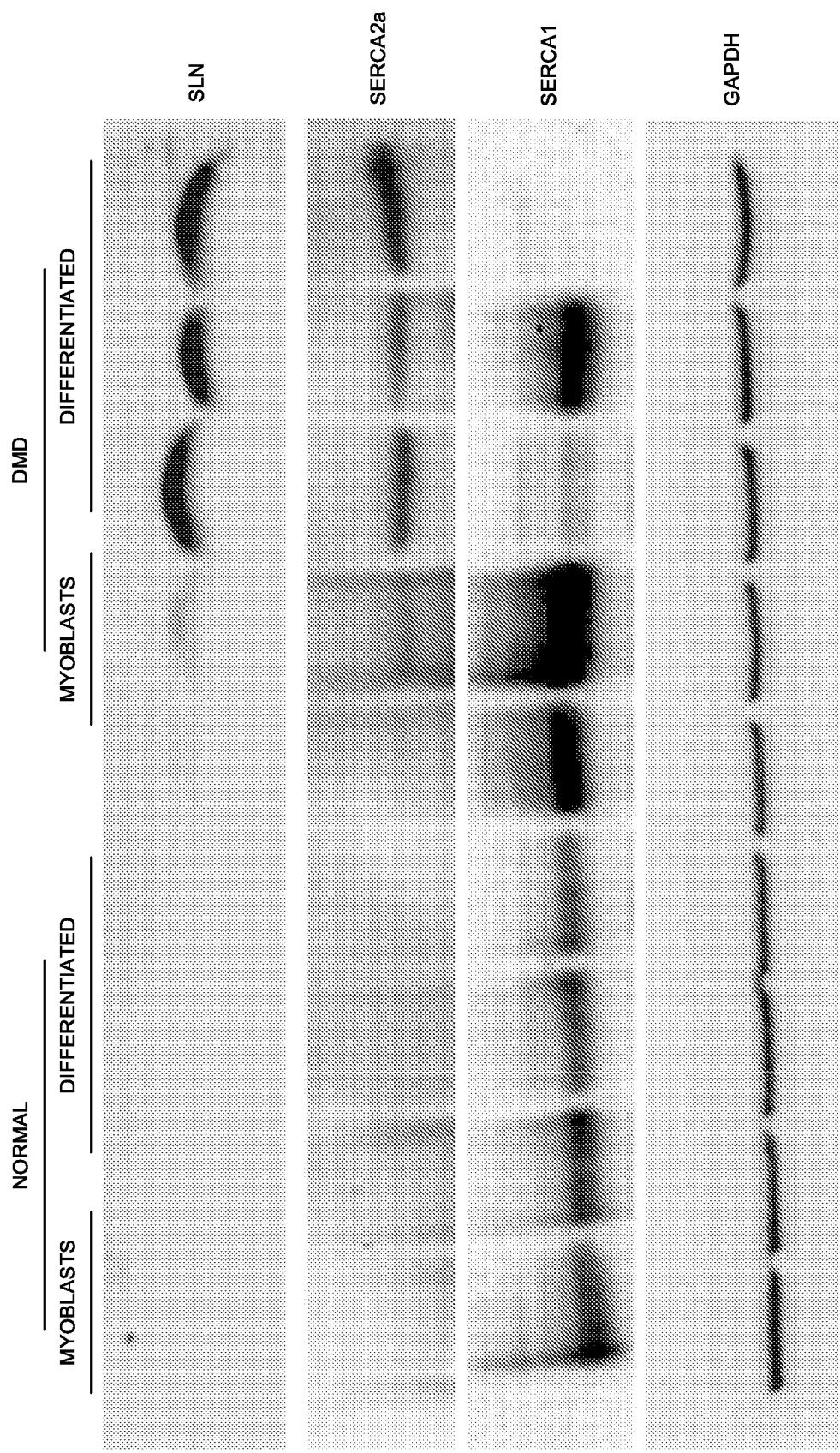
FIG. 16 shows SLN protein levels were increased in canine dystrophic myoblasts and in 3 days differentiated myotubes compared to normal (control) canine myoblasts. SERCA1, a predominant isoform is decreased and SERCA2a is increased in the dystrophic myotubes in comparison to normal myotubes.
Figure 17:
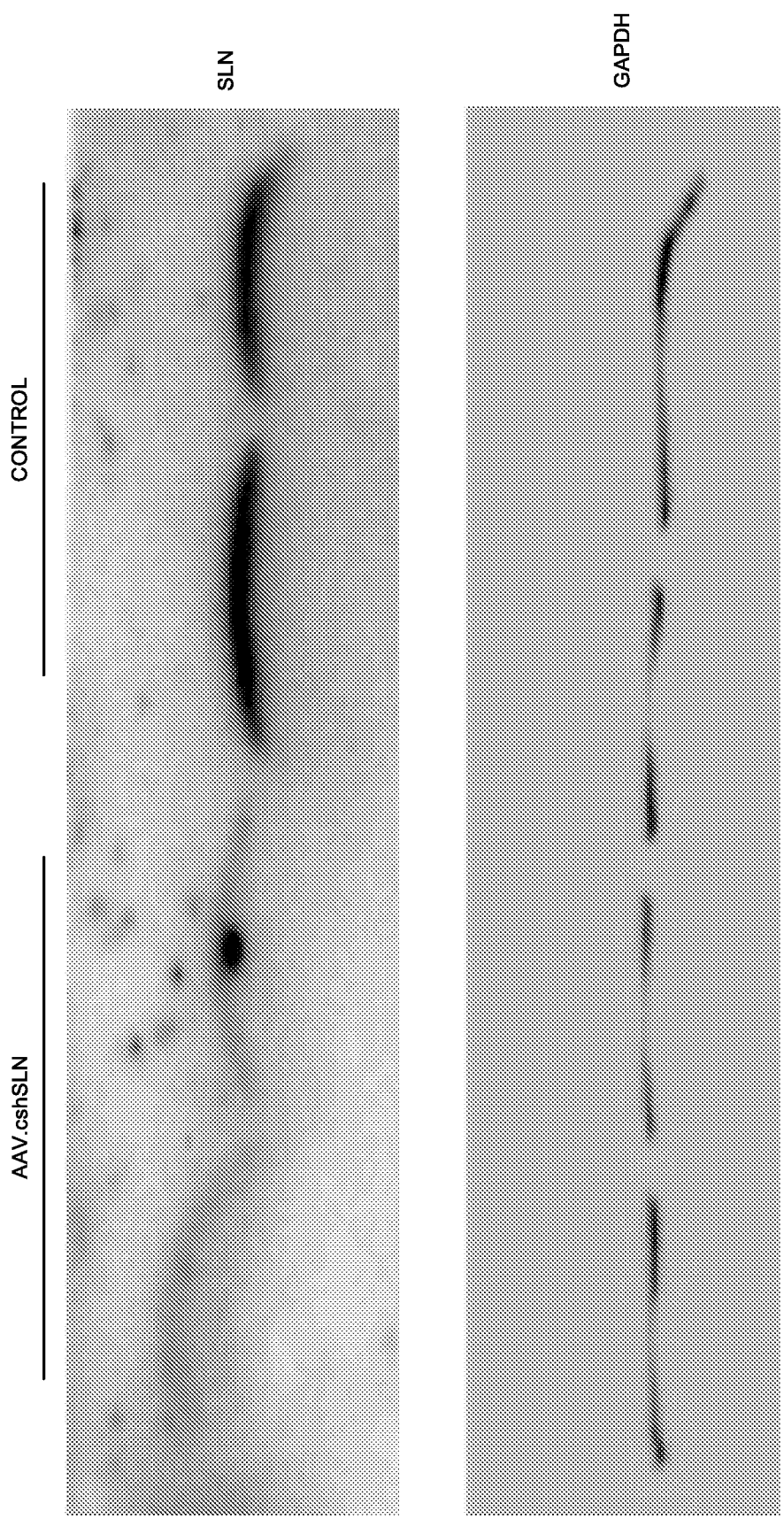
FIG. 17 shows treating with AAV 9 expressing canine specific SLN shRNA (AAV9.cshSEV) reduces SLN protein levels in 3 days differentiated canine dystrophic myotubes. GAPDH was used as loading controls.

SLN is upregulated in the dystrophic canine myoblasts (FIG. 16). The canine specific shSLN (5'-ctgtttctcaacttcactattgtttcaagagaacaatagtgaagttgagaaacag-3') (SEQ ID NO:5) expressed using AAV9 reduced SLN expression in dystrophic canine myoblasts (FIG. 17).

Example 3

Combined AAV9.shSLN and AAV9µdys Gene Therapy

Reducing SLN expression was beneficial in mitigating DMD; however, this approach will not correct the lack of dystrophin. AAV-mediated micro-dystrophin (µ-dys) treatment can restore the dystrophin function. However, studies from many groups have shown that µ-dys cannot normalize contractile force in dystrophic muscles. A combined SLN reduction and µ-dys therapy may overcome these problems and result in better protection. Therefore, 1 month-old mdx and mdx:utr-/- mice are treated with AAV9.shSLN and Y731F AAV9.ΔR2 µDys (Yue et al. (2015) Hum Mol Genet. 24(20):5880-90) at the doses of 1×10$^{11}$ vg and 5×10$^{12}$ vg, respectively, per mouse via tail vein injection. These mice are evaluated 12 weeks after injection for structural and functional corrections as described above. The data are compared with mice treated with single vectors.

A range between 1×10¹¹ and 1×10¹² vg of AAV9.shSLN is expected with a high efficacy in reducing SLN expression in vivo without any nonspecific toxicity. It is expected that combined AAV9.shSLN and AAV9.µ-dys gene therapy should yield better structural and functional protection than either therapy alone.

Increased longevity for AAV9.shSLN and AAV9.shSLN/AAV9.µ-dys treated mdx:utr−/− mice is expected. Therefore, the treatment time for mdx:utr−/− mice is increased and they are examined depending on their survival period.

As used herein, the terms "microdystrophin," "microdystrophin," and "µ-dys" generically mean any dystrophin sequence which lacks a major portion of the coding sequence. Any suitable microdystrophin sequence can be used in vectors, compositions, and methods as described herein. In humans, microdystrophin therapy typically includes a human µ-dys or human optimized µ-dys (e.g., Kornegay et al., Mol. Ther. 18, 1501-1508, 2010), and is typically for patients with dystrophin mutations between exons 18-58. Because several studies have shown that the N-terminal actin binding domain and the C-terminal domain of dystrophin are necessary for the dystroglycan complex (DGC) assembly and are important for the function of dystrophin protein, in a typical embodiment, a micro-dystrophin gene is synthesized containing these domains and placed under a muscle-specific promoter and delivered and expressed using rAAV as described above. One example of a human micro-dystrophin sequence is that described in J. R. Mendell et al., N Engl J Med. 2010 Oct. 7; 363(15):1429-37, in which an rAAV vector encoded the amino-terminal actin binding domain (ABD), 5 rod repeat domains (R1, R2, R22, R23 and R24), 3 hinge domains (H1, H3 and H4), and the cysteine-rich (CR) domain of the human dystrophin gene. Such a micro-dystrophin sequence can be used in the vectors, compositions and methods described herein. The human dystrophin gene sequence is known and available.

Example 4

Human shSLN Sequences

Examples of human shSLN sequences that may be used for decreasing SLN expression or activity in a human subject (e.g., a subject with DMD or DMD and cardiomyopathy) and preventing, ameliorating, or treating DMD and in some embodiments, also cardiomyopathy, include:

shRNA 1:
(SEQ ID NO: 6)
ctgtgaaaatggggataaacacc TTCAAGAGA ggtgtttatccccatt ttcacag shRNA2:
(SEQ ID NO: 7)
GTCTTGATTACGGTTATTCTTCTCGAGAAGAATAACCGTAATCAAGAC.

Figure 18A:
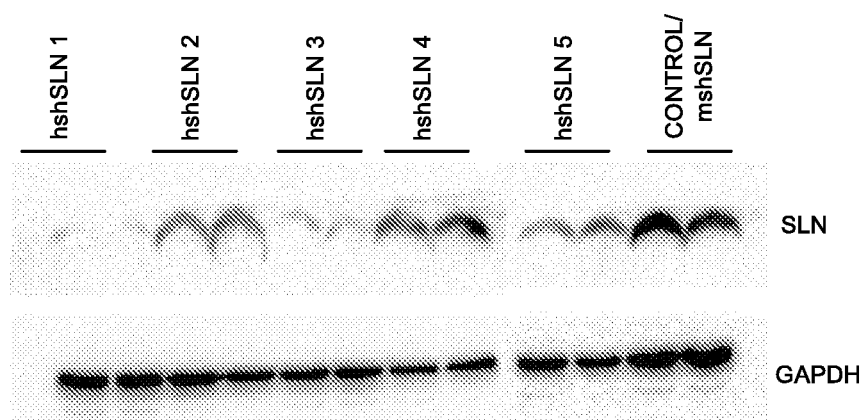
FIG. 18(A) (Western blot analysis) and 18(B) (quantitation) show the effect of various short-hairpin RNA on reducing human SLN expression in co-transfection experiments in HEK293 cells.
Figure 18B:
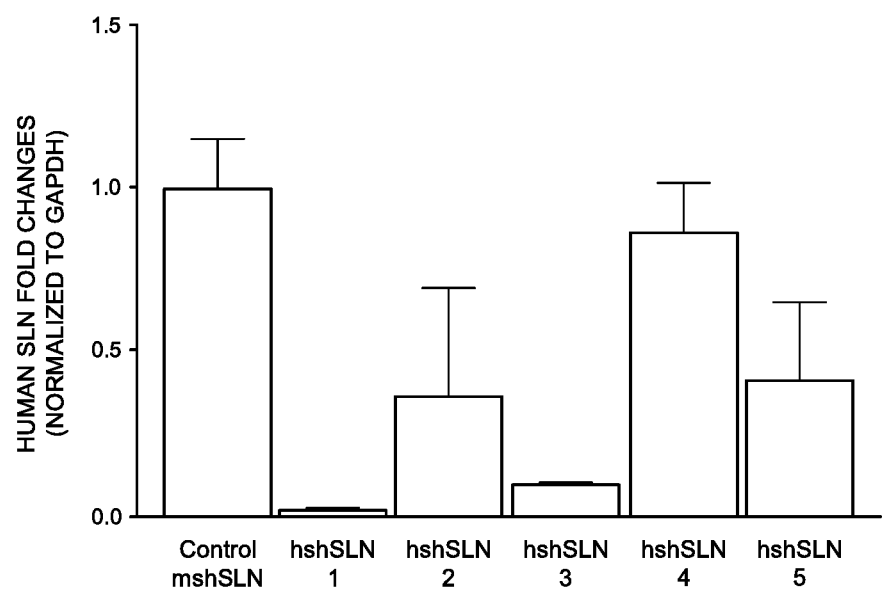

Additional human shSLN sequences include those having, for example, 85% or more (e.g., 90%, 95%, 99%) sequence identity with SEQ ID NO: 6 or SEQ ID NO:7.

shRNA sequences specific for human SLN were identified and tested. These sequences effectively reduced human SLN expression in cell culture systems. In order to select potential shRNA specific for human SLN (hshSLN), several small interfering RNA sequences cloned in the shRNA expression plasmid (pLKO.1 puro vector, Sigma-Aldrich) were screened by co-transfection of HEK293, a human cell line with a human SLN cDNA construct. For controls, the plasmid expressing mouse shSLN (mshSLN), which has no effect on human SLN expression, was transfected along with human SLN cDNA. Five different short-hairpin sequences, which effectively reduced human SLN protein levels, were found. Table 3 shows the DNA sequence information for these five shRNA sequences. Among the five shRNA sequences, hshSLN1 and hshSLN3 had very high efficacy in reducing the SLN protein levels. These two shRNAs reduced the SLN protein levels more than 90% (FIG. 18). The hshSLN2 and hshSLN5 reduced the SLN protein levels to ~50% and shSLN4 reduced ~30% (FIG. 18). Based on these information, the order of preferences for shRNAs specific for human SLN are:

1) hshSLN1
2) hshSLN3
3) hshSLN2
4) hshSLN5
5) hshSLN4

Additional human shSLN sequences include those having, for example, 85% or more (e.g., 90%, 95%, 99%) sequence identity with SEQ ID NO:7, SEQ ID NO:8, SEQ ID NO:9, SEQ ID NO:10, or SEQ ID NO:11.

TABLE 3

Human short-hairpin RNA sequences

| shRNA # | Sequence |
| --- | --- |
| hshSLN1 | GTCTTGATTACGGTTATTCTTCTCGAGAAGAATAACCGTAATCAAGAC (SEQ ID NO:7) |
| hshSLN2 | GTTATTCTTATGTGGCTCCTTCTCGAGAAGGAGCCACATAAGAATAAC (SEQ ID NO:8) |
| hshSLN3 | TCTCAACTTCACTATTGTCTTCTCGAGAAGACAATAGTGAAGTTGAGA (SEQ ID NO:9) |
| hshSLN4 | ACTATTGTCTTGATTACGGTTCTCGAGAACCGTAATCAAGACAATAG (SEQ ID NO:10) |
| hshSLN5 | GCTCCTTGTGAGGTCCTATCACTCGAGTGATAGGACCTCACAAGGAGC (SEQ ID NO:11) |

Example 5

Human SLN mRNA Sequence (SEQ ID NO: 12)
  1 agtccagaca gcctgggagg ggagaaggag ttggagctca agttggagac agcgaggaga 61 aacctgccat agccagggtg tgtctttgat cctcttcagg aggtgaggag aagccagagg 121 tcctggtgt gccctcagaa atctgcctgc agttctcacc aagccgctgt gaaaatgggg 181 ataaacaccc gggagctgtt tctcaacttc actattgtct tgattacggt tattcttatg

```
241   tggctccttg tgaggtccta tcagtactga gaggccatgc catggtcctg ggattgactg 301   agatgctccg gagctgcctg ctctatgccc tgagacccca ctgctgtcat tgtcacagga 361   tgccattctc catccgaggg cacctgtgac ctgcactcac aatatctgct atgctgtagt 421   gctaggattg attatgtgtt ctccaaagat gctgctccca agggctgcca agtgtttgcc 481   agggaacggt agatttattc cccaactctt aactgaaaat gtgttagaca agccacaaag 541   ttaaaattaa actggattca tgatgatgta ggattgttac aagcccctga tctgtctcac 601   cacacatccc ttcaacccac acggtctgca accaaactct aattcaacct gccagaagga 661   atgttagagg aagtctttgt cagcccttat agctatcatg tgaataaagt taagtcaact 721   tcaaaacaa aaaaaaaa
```

Other Embodiments

All nucleic acids, nucleic acid names, genes, gene names, and gene products disclosed herein are intended to correspond to homologs from any species for which the compositions, viruses, vectors, kits, and methods disclosed herein are applicable. Thus, the terms include, but are not limited to, nucleic acids, genes and gene products from humans, mice and dogs. It is understood that when a nucleic acid, gene or gene product from a particular species is disclosed, this disclosure is intended to be exemplary only, and is not to be interpreted as a limitation unless the context in which it appears clearly indicates. Any improvement may be made in part or all of the compositions, viruses, vectors, kits, and method steps. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of preventing or treating Duchenne Muscular Dystrophy (DMD) in a subject comprising administering to the subject a recombinant virus comprising a recombinant viral vector comprising a heterologous polynucleotide sequence comprising a nucleic acid sequence encoding a shRNA specific for SLN, or a composition comprising the recombinant virus.

2. The method of claim 1, wherein the subject is a mammal and the recombinant virus is rAAV.

3. The method of claim 1, wherein administration of the recombinant virus or the composition comprising the recombinant virus prevents or treats associated cardiomyopathy in the subject.

4. The method of claim 1, wherein the recombinant virus or the composition comprising the recombinant virus is administered to the subject prior to onset of DMD symptoms or pathology.

5. The method of claim 1, wherein the subject is administered the recombinant virus or the composition comprising the recombinant virus via injection.

* * * * *